(12) United States Patent
Ernst et al.

(10) Patent No.: US 6,541,425 B1
(45) Date of Patent: Apr. 1, 2003

(54) RETARDING FORMULATIONS OF ACTIVE SUBSTANCES USED FOR PLANT PROTECTION

(75) Inventors: Andreas Ernst, Worms (DE); Matthias Bratz, Limburgerhof (DE); Karl-Heinrich Schneider, Kleinkarlbach (DE); Armin Lange, Heidelberg (DE); Thomas Kessler, Schifferstadt (DE); Klaus Schelberger, Gönnheim (DE); Siegfried Strathmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/674,182

(22) PCT Filed: Apr. 22, 1999

(86) PCT No.: PCT/EP99/02698

§ 371 (c)(1),
(2), (4) Date: Oct. 27, 2000

(87) PCT Pub. No.: WO99/56540

PCT Pub. Date: Nov. 11, 1999

(30) Foreign Application Priority Data

Apr. 30, 1998 (DE) .......................................... 198 19 282

(51) Int. Cl.⁷ .......................... A01N 37/34; A01N 3/02; A01N 63/00

(52) U.S. Cl. ........................ 504/312; 504/116; 504/118; 504/141

(58) Field of Search ................................ 424/405, 400; 504/117, 116, 118, 141, 312

(56) References Cited

U.S. PATENT DOCUMENTS

| | | | | |
|---|---|---|---|---|
| 4,400,374 A | 8/1983 | Cardaralle | .................... | 424/78 |
| 4,743,448 A | 5/1988 | Bahadir et al. | .............. | 424/405 |
| 4,801,460 A | 1/1989 | Goertz et al. | ................ | 424/465 |
| 4,880,585 A | 11/1989 | Klimesch et al. | ........... | 264/141 |
| 5,643,590 A | 7/1997 | Cannelongo | ................ | 424/406 |
| 5,645,847 A | 7/1997 | Cannelongo | ................ | 424/408 |

FOREIGN PATENT DOCUMENTS

| | | |
|---|---|---|
| AU | 712017 | 2/1998 |
| CA | 2082549 | 5/1989 |
| EP | 142 658 | 5/1985 |
| EP | 369 612 | 5/1990 |
| EP | 542 081 | 5/1993 |
| EP | 843 963 | 5/1998 |
| JP | 7 242502 | 9/1995 |
| WO | WO 97/46094 | 12/1997 |

OTHER PUBLICATIONS

Tashima et al. "Effect of Controlled Release Granule on Behavior of SSF–126 in Paddy Water, Paddy Soil and Rice Plant" J. Pesticide Sci. vol. 22 (1997) pp. 90–94.

Primary Examiner—Alton N Pryor
(74) Attorney, Agent, or Firm—Keil & Weinkauf

(57) ABSTRACT

Solid formulation of a crop protection product can be obtained by melt extrusion and shaping of a mixture consisting of:

- 0.1–80% by wt. of an active ingredient which can be used in crop protection, or of a combination of such active ingredients,
- 10–80% by wt. of at least one mineral filler,
- 0–20% by wt. of inorganic or organic additives, and
- to 100% by wt. of at least one thermoplastic water-insoluble polymer

9 Claims, 12 Drawing Sheets

RETARDING FORMULATIONS OF ACTIVE SUBSTANCES USED FOR PLANT PROTECTION

This application is a 371 of PCT/EP99/02698 filed Apr. 22, 1999.

The present invention relates to a solid formulation of a crop protection product with delayed release of the active ingredient, obtainable by preparing a melt comprising:

0.1–80% by wt. of an active ingredient which can be used in crop protection, or of a combination of such active ingredients, 10–80% by wt. of at least one mineral filler, 0–20% by wt. of inorganic or organic additives, and to 100% by wt. of at least one thermoplastic water-insoluble polymer, the total of all constituents equaling 100% by weight, and subsequent shaping.

The invention furthermore relates to a process for the preparation of a solid formulation of a crop protection product, which comprises melting at least one active ingredient, at least one mineral filler and, if appropriate, inorganic or organic additives with at least one thermoplastic, water-insoluble polymer (solubility<100 mg per 1 of water at 20° C.) in an extruder to give a thermoplastic mixture and subsequently subjecting this mixture to shaping, either in the hot or cold state.

The invention furthermore relates to a process which comprises using in solid form such a solid formulation of a crop protection product for controlling phytopathogenic fungi, undesired vegetation, undesired attack by insects or mites, and/or for regulating plant growth, and allowing it to act on plants, their environment or on seed. Such solid formulations furthermore release the active ingredient(s) which it comprises in a controlled and slow manner (complete release within several days up to some months) into the environment (soil, aqueous medium, plants). This leads to a biological availability over a prolonged period to suit the respective purpose. For example, this is necessary for active ingredients which are insufficiently persistent in soil and/or plant, for active ingredients which are phytotoxic to the crop plant, or else for applications where it is required that the availability or release of active ingredient extends over a prolonged period.

Formulations comprising active ingredient which are prepared by melt extrusion are generally known. Extruding and subsequent shaping of melts of water-soluble polymers, preferably copolymers of vinylpyrrolidone, which contain active ingredient are described in EP-A 240904 and EP-A 240906.

WO 94/08455 describes the coextrusion of crop protection products with polyvinylpyrrolidone and subsequent cooling, crushing and grinding. The ground extrudate disperses rapidly and finely in water and is suitable for spray applications.

There are furthermore known solid formulations of crop protection products which are prepared by melt extrusion with subsequent shaping and which allow a controlled, slow release of pesticides.

WO 91/03940 describes biodegradable pesticide-comprising matrices, their preparation by means of melt extrusion with subsequent shaping, and their use for the controlled release of pesticides. In addition to synthetic polymers (<25%, mainly ethylene/vinyl acetate copolymers), starch and starch derivatives are subjected to melt extrusion together with the respective active substances (carbosulfan inter alia) with addition of water and glycerol to give the matrix. Depending on the formula, the matrices release the active ingredients in water within weeks or months.

WO 95/28835 describes the preparation of agrochemical formulations with hydrophobic and hydrophilic waxes. Active ingredient, carnauba wax and polyethylene glycol are subjected to melt extrusion, ground and graded. The 500–1000 μm fraction is released in water. Depending on the composition, 14–100% of the active ingredients are released after 10 hours.

U.S. Pat. No. 5,643,590 describes insecticidal compositions whose mammalian toxicity is markedly reduced. In a multi-step process, pesticides together with PVC, stabilizer, plasticizer and mineral additive are mixed intimately at 75–110° C., and the mixture is cooled to 70° C., transferred into an extruder, extruded at 150–180° C. and subsequently pelleted. The pellets, which do not dust, exhibit a markedly reduced toxicity to mammals and a prolonged activity (100% worm control over 10 weeks).

DE 19 622 355 describes the preparation by melt extrusion and injection molding of shaped articles which exhibit controlled release. The crop protection agent—together with a vinyl acetate polymer which is insoluble in water and a water-soluble polymer (polyvinyl acetate/vinylpyrrolidone)—is subjected to melt extrusion and granulation.

Formulations based on synthetic polymers and starch (WO 91/03940) can be plastified homogeneously and granulated to give dust-free granules in a simple manner—i.e., inter alia, without addition of water and/or glycerol—only if the polymer content is high (>60%) and rapidly show signs of decomposition since the starch is sensitive to heat and shearing forces. Also, such formulations swell and exhibit low density and thus only show insufficient sedimentation in water or soils flooded with water.

While formulations based on hydrophobic and hydrophilic waxes (WO 95/28835) are easy to prepare by simply melting them together with the active ingredient, they are not easy to process (for example extrusion granulation, hot cutting) and are not dimensionally stable upon heat aging (14 days at 54° C.) as a result of the wax-like consistency. Moreover, formulations made of stearic acid or stearyl alcohol and PEG do not sediment in water (density<1 g/ml).

U.S. Pat. No. 5,643,590 describes a complicated multi-step process in which pesticides are mixed intimately at 75–110° C. with PVC, stabilizer, plasticizer and mineral additive, the mixture is cooled to 70° C., transferred into an extruder and extruded at 150–180° C., and the extrudate is subsequently pelleted. The lack of thermal stability of a large number of active ingredients does not allow high temperature stress because of the danger of decomposition. Moreover, the manufacturing process should be as simple as possible.

In DE 19 622 355, crop protection agents are subjected to melt extrusion and granulation together with a vinyl acetate polymer which is insoluble in water and a water-soluble polymer (polyvinyl acetate/vinylpyrrolidone). Due to low glass transition temperatures, formulations based on polyvinyl acetate polymers exhibit insufficient heat resistance. Upon heat aging (14 days at 54° C.), granulated melt extrudates made of polyvinyl acetate and polyvinylpyrrolidone coalesce to form a coherent mass.

The problems are insufficient heat and storage stability, inadequate sedimentation, poor granulation properties, inadequate homogeneity of the melt, and complicated and expensive production.

It is an object of the present invention to provide a solid, storage-stable, slow-releasing crop protection formulation which settles in water, can be granulated and can be prepared readily from inexpensive components by subjecting a mixture of solids to melt extrusion, followed by shaping.

We have found that this object is achieved by the composition described at the outset and the process for its preparation.

In general, suitable active ingredients are those which do not undergo decomposition under the processing temperatures when preparing the melt. Preferred substances are those which are solid at room temperature since these are easier to mix and meter. However, the use is not restricted to solid active ingredients since even liquid active ingredients can be processed by means of a solid matrix to give a solid, heat-resistant and storage-stable formulation.

The amount of active ingredient components in the total formulation may vary within wide limits, depending on efficacy, release rate and processability. Thus, the active ingredient content may range from 0.1–80% by weight, preferably from 0.5–40% by weight, especially preferably from 1–20% by weight, based on the total formulation. The only condition is that the formulation is still thermoplastically processable.

Crop protection agents which may be mentioned are fungicides, herbicides, insecticides and growth regulators. Combinations are also possible.

The following list of herbicides identifies possible active ingredients, but is not to be understood as being restricted to these.

b1 1,3,4-Thiadiazoles:
  buthidazole, cyprazole
b2 Amides:
  allidochlor (CDAA), benzoylprop-ethyl, bromobutide, chlorthiamid, dimepiperate, dimethenamid, s-dimethenamid, diphenamid, etobenzanid (benzchlomet), flamprop-methyl, fluthiamide, fosamin, isoxaben, monalide, naptalame, pronamid (propyzamid), propanil
b3 Aminophosphoric acids:
  bilanafos, (bialaphos), buminafos, glufosinate-ammonium, glyphosate, sulfosate
b4 Aminotriazoles:
  amitrol
b5 Anilides:
  anilofos, mefenacet
b6 Aryloxyalkanoic acid [sic]:
  2,4-D, 2,4-DB, clomeprop, dichlorprop, dichlorprop-p, dichlorprop-p (2,4-DP-P), fenoprop (2,4,5-TP), fluoroxypyr, MCPA, MCPB, mecoprop, mecoprop-P, napropamide, napropanilide, triclopyr, N-(1-cyano-1,2-dimethylpropyl)-2-(2,4-dichloro-phenoxy) propionamides [sic]
b7 Benzoic acids:
  chloramben, dicamba
b8 Benzothiadiazinones:
  bentazone
b9 Bleachers:
  clomazone (dimethazone), diflufenican, fluorochloridone, flupoxam, fluridone, pyrazolate, sulcotrione (chlormesulone), isoxaflutole, isoxachlortole, mesotrione
b10 Carbamates:
  asulam, barban, butylate, carbetamid, chlorbufam, chlorpropham, cycloate, desmedipham, di-allate, EPTC, esprocarb, molinate, orbencarb, pebulate, phenisopham, phenmedipham, propham, prosulfocarb, pyributicarb, sulf-allate (CDEC), terbucarb, thiobencarb (benthiocarb), tiocarbazil, tri-allate, vernolate
b11 Quinoline [sic] acids:.
  quinclorac, quinmerac
b12 Chloroacetanilides:
  acetochlor, alachlor, butachlor, butenachlor, diethatyl ethyl, dimethachlor, metazachlor, metolachlor, pretilachlor, propachlor, prynachlor, terbuchlor, thenylchlor, xylachlor, s-metolachlor
b13 Cyclohexenones:
  alloxydim, tepraloxydim, clethodim, cloproxydim, cycloxydim, sethoxydim, tralkoxydim, 2-{1-[2-(4-chlorophenoxy)-propyloxyimino]butyl}-3-hydroxy-5-(2H-tetrahydrothiopyran-3-yl)-2- cyclohexen-1-one, butroxydim, clefoxydim
b14 Dichloropropionic acids:
  dalapon
b15 Dihydrobenzofurans:
  ethofumesate
b16 Dihydrofuran-3-ones:
  flurtamone
b17 Dinitroanilines:
  benefin, butralin, dinitramin, ethalfluralin, fluchloralin, isopropalin, nitralin, oryzalin, pendimethalin, prodiamine, profluralin, trifluralin
b18 Dinitrophenols:
  bromofenoxim, dinoseb, dinoseb-acetate, dinoterb, DNOC
b19 Diphenyl ethers:
  acifluorfen-sodium, aclonifen, bifenox, chlornitrofen (CNP), difenoxuron, ethoxyfen, fluorodifen, fluoroglycofen-ethyl, fomesafen, furyloxyfen, lactofen, nitrofen, nitrofluorfen, oxyfluorfen
b20 Dipyridylenes:
  cyperquat, difenzoquat-methylsulfate, diquat, paraquat dichloride
b21 Ureas:
  benzthiazuron, buturon, chlorbromuron, chloroxuron, chlortoluron, cumyluron, dibenzyluron, cycluron, dimefuron, diuron, dymron, ethidimuron, fenuron, fluormeturon, isoproturon, isouron, karbutilate, linuron, methabenzthiazuron, metobenzuron, metoxuron, monolinuron, monuron, neburon, siduron, tebuthiuron, trimeturon
b22 Imidazoles:
  isocarbamide
b23 Imidazolinones:
  imazamethapyr, imazapyr, imazaquin, imazethabenz-methyl (imazame), imazethapyr, imazapic
b24 Oxadiazoles:
  methazole, oxadiargyl, oxadiazon
b25 Oxiranes:
  tridiphane
b26 Phenols:
  bromoxynil, ioxynil
b27 Phenoxyphenoxypropionic esters:
  clodinafop, cloquintocet, cyhalofop-butyl, diclofop-methyl, fenoxaprop-ethyl, fenoxaprop-p-ethyl, fenthiapropethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl, quizalofop-tefuryl b28 Phenylacetic acids:
  chlorfenac (fenac)
b29 Phenylpropionic acids:
  chlorophenprop-methyl
b30 Protoporphyrinogen IX oxydase inhibitors:
  benzofenap, cinidon-ethyl, flumiclorac-pentyl, flumioxazin, flumipropyn, flupropacil, fluthiacet-methyl, pyrazoxyfen, sulfentrazone, thidiazimin, carfentrazone
b31 Pyrazoles:
  nipyraclofen, ET 751
b32 Pyridazines:
  chloridazon, maleic hydrazide, norflurazon, pyridate
b33 Pyridinecarboxylic acids:
  clopyralid, dithiopyr, picloram, thiazopyr, diflufenzopyr
b34 Pyrimidyl ethers:
  pyrithiobac-acid, pyrithiobac-sodium, KIH-2023, KIH-6127, pyribenzoxym
b35 Sulfonamides:
  flumetsulam, metosulam
b36 Sulfonylureas:
  amidosulfuron, azimsulfuron, bensulfuron-methyl, chlorimuron-ethyl, chlorsulfuron, cinosulfuron, cyclosulfamuron, ethametsulfuron methyl, ethoxysulfuron, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]carbonyl]-2-(trifluoromethyl) benzene sulfonamide, sulfosulfuron, idosulfuron
b37 Triazines:
  ametryn, atrazine, aziprotryn, cyanazine, cyprazine, desmetryn, dimethamethryn, dipropetryn, eglinazine-ethyl, hexazinon, procyazine, prometon, prometryn, propazine, secbumeton, simazine, simetryn, terbumeton, terbutryn, terbutylazine [sic], trietazine
b38 Triazinones:
  ethiozin, metamitron, metribuzin
b39 Triazolecarboxamides:
  triazofenamid
b40 Uracils:
  bromacil, lenacil, terbacil
b41 Various:
  benazolin, benfuresate, bensulide, benzofluor, butamifos, cafenstrole, chlorthal-dimethyl (DCPA), cinmethylin, dichlobenil, endothall, fluorbentranil, mefluidide, perfluidone, piperophos, flucabazone, oxaciclomefone (MY 100)

The following list of compounds which have growth-regulatory activity identifies possible active ingredients from this group but is not to be understood as being restricted to these.
  Compounds with growth-regulatory activity, such as
  1-naphthylacetamide, 1-naphthylacetic acid, 2-naphthyloxyacetic acid, 3-CPA, 4-CPA, ancymidol, anthraquinone, BAP, butifos; tribufos, butralin, chlorflurenol, chlormequat, clofencet, cyclanilide, daminozide, dicamba, dikegulac sodium, dimethipin, chlorfenethol, etacelasil, ethephon, ethychlozate, fenoprop, 2,4,5-TP, fluoridamid, flurprimidol, flutriafol, gibberellic acid, gibberillin [sic], guazatine, imazalil, indolylbutyric acid, indolylacetic acid, karetazan, kinetin, lactidichlor-ethyl, maleic hydrazide, mefluidide, mepiquat-chloride, naptalam, paclobutrazole, prohexadione calcium, quinmerac, sintofen, tetcyclacis, thidiazuron, triiodobezoic [sic] acid, triapenthenol, triazethan, tribufos, trinexapacethyl, uniconazole.

The following list of insecticides identifies possible active ingredients, but is not to be understood as being restricted to these.
  Neonicotinoids/chloronicotinyl compounds:
    imidacloprid, acetamiprid, nitenpyram, thiacloprid, thiamethoxam, MIT-446
  organophosphates such as
    acephate, azinphos-methyl, chlorpyrifos, dimethoate, disulfoton fosthiazate, methamidophos, methidathion, methyl-parathion, oxydemeton-methyl, phorate, phosalone,
    phosmet, profenofos, trichlorfon, malathion, phosphamidon, monocrotophos, fenitrothion, diazinon, EPN
  carbamates such as
    alanycarb, aldicarb, benfuracarb, carbofuran, carbosulfan, furathiocarb, methomyl, oxamyl, pirimicarb, thiodicarb, fenobucarb
  pyrethroids such as
    bifenthrin, cyfluthrin, cypermethrin, deltamethrin, esfenvalerate,
    fenpropathrin, lambda-cyhalothrin, permethrin, tau-fluvalinate, tralomethrin, zeta-cypermethrin
  urea derivatives such as
    diflubenzuron, flucycloxuron, flufenoxuron, hexaflumuron, lufenuron,
    novaluron, triflumuron
  juvenuids [sic] such as
    buprofezin, diofenolan, fenoxycarb, pyriproxifen, methoxyfenozide, tebufenozide
  Various such as
    abamectin, spinosad, amitraz, cartap, chlorfenapyr, diafenthiuron, fipronil, fudioxonil
    pyridaben, tebufenpyrad, fenazaquin, fenpyroximate, thiocyclam, silafluofen The following may be mentioned as being especially preferred:

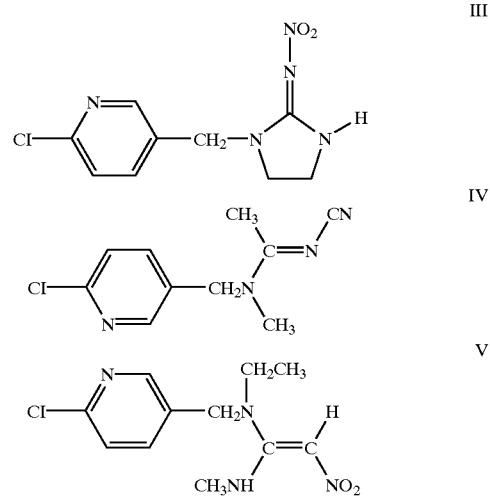

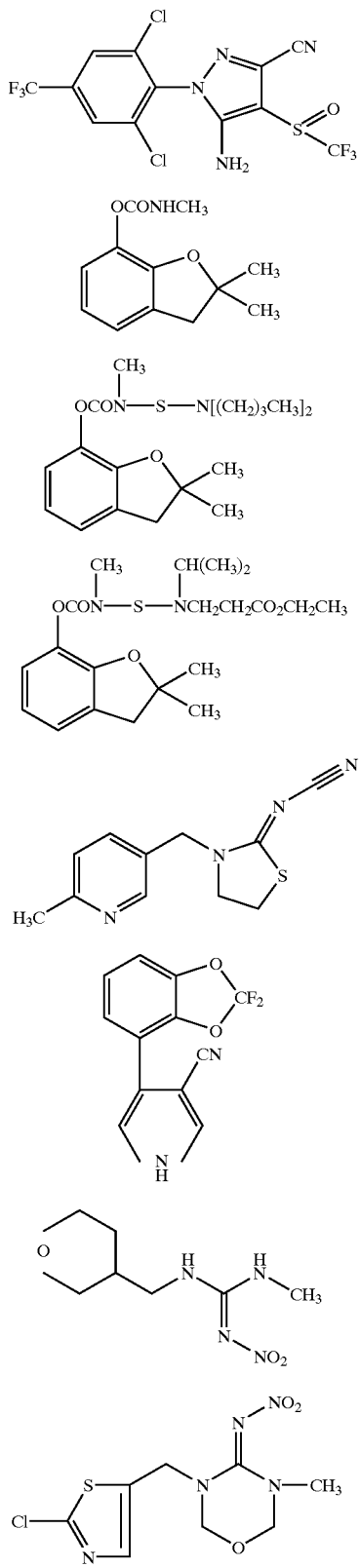

The insecticides of the formulae III to IX are commercially available under the trade names mentioned hereinbelow in brackets:

III: EP-A 192,060, common name: imidacloprid (trade name: Admire®, Gaucho®, Bayer)
IV: common name: acetamiprid (trade name Mospilan®, Nippon Soda)
V: CAS RN 120738-89-8, common name: nitenpyram (trade name: Bestgard®, Takeda Chemicals);
VI: Colliot et al., Proc. Br. Conf. Dis. 1992, 1, 29, common name: fipronil (trade name: Regent®, Rhone-Poulenc);
VII: U.S. Pat. Nos. 3,474,170; 3,474,171 and DE-C 1,493, 646; common name: carbofuran (trade name Curaterr®, Bayer; Furadan®, FMC);
VIII: Proc. Br. Crop Prot. Conf., 1979, Vol.2, 557, common name:carbosulfan (trade name: Marshall®, FMC);
IX: FR-A 2,489,329; Proc. Int. Congr. Plant Prot. 10th, 1983, 2, 360, common name: benfuracarb (trade name: Oncol®, Otsuka, Furacon®, Siapa Chem.)
X: CAS RN 111 988-49-9, common name: thiacloprid (developed by Bayer);
XI: CAS RN [131341-86-1], common name: fludioxonil, (trade name: Celest®, Ciba Geigy), 4-(2,2-difluoro-1,3-benzodioxol-7yl)-1H-pyrrole-3-carbonitrile
XII: Tefuranitde (proposed), MTI-466, The 1998 Brighton Conference "Pest and Diseases", Conference Proceedings, Vol 1, page 81
XIII: Thiamethoxam (CGA 293343), The 1998, Brighton Conference "Pest and Diseases", Conference Proceedings, Vol 1, page 27

The following list of fungicides identifies possible active ingredients, but is not to be understood as being restricted to these.

Fungicides from the following classes sulfur, dithiocarbamates and their derivatives such as iron (III) dimethyldithiocarbamate, zinc dimethyldithiocarbamate, zinc ethylenebis (dithiocarbamate), manganese ethylenebis (dithiocarbamate), manganese zinc ethylenediaminebis (dithiocarbamate), tetramethylthiuram disulfides [sic], ammonia complex of zinc N,N-ethylenebis (dithiocarbamate), ammonia complex of zinc N,N'-propylenebis(dithiocarbamate), zinc N,N'-propylenebis (dithiocarbamate), N,N'-polypropylenebis (thiocarbamoyl)disulfide;

nitro derivatives such as dinitro-(1-methylheptyl)phenyl crotonate, 2-sec-butyl-4,6-dinitrophenyl-3,3-dimethyl acrylate, 2-sec-butyl-4,6-dinitrophenyl isopropyl carbonate, diisopropyl 5-nitroisophthalate;

heterocyclic substances such as 2-heptadecyl-2-imidazoline acetate, 2,4-dichloro-6-(o-chloroanilino)-s-triazine, O,O-diethyl phthalimidophosphonothioate, 5-amino-1-[bis (dimethylamino)-phosphinyl]-3-phenyl-1,2,4-triazole, 2,3-dicyano-1,4-dithioanthraquinone, 2-thio-1,3-dithiolo [4,5-b]quinoxaline, methyl 1-(butylcarbamoyl)-2-benzimidazolecarbamate, 2-methoxycarbonylaminobenzimidazole, 2-(2-furyl) benzimidazole, 2-(thiazol-4-yl)benzimidazole, N-(1,1,2, 2-tetrachloroethylthio)-tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-mercaptomethylthiobenzothiazole, 1,4-dichloro-2,5-dimethoxybenzene, 4-(2-chlorophenylhydrazono)-3-methyl-5-isoxazolone, pyridin-2-thiol 1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3- carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholin-2,2,2-trichloroethyl acetal, piperazin-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]cis-2,6-dimethyl-morpholine, N-[3-(p-tert-butylphenyl)-2-methylpropyl] piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, a-(2-chlorophenyl)-a-(4-chlorophenyl)-5-pyrimidinemethanol [sic], 5-butyl-2-dimethylamino-4-hydroxy-6-methylpyrimidine, bis-(p-chlorophenyl)-3-pyridinemethanol, 1,2-bis(3-ethoxycarbonyl-2-thioureido)benzene, 1,2-bis(3-methoxycarbonyl-2-thioureido)benzene, anilinopyrimidines such as N-(4,6-dimethylpyrimidin-2-yl)aniline, N-[4-methyl-6-(1-propynyl)pyrimidin-2-yl]aniline, N-[4-methyl-6-cyclopropylpyrimidin-2-yl]aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxyphenyl) acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, DL-methyl N-(2,6-dimethylphenyl)-N-furoyl-(2)-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl)-1,3-oxazolidine-2,4-dione [sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-a-(1H-1,2,4-triazolyl-1-methyl)benzhydryl [sic] alcohol, N-(3-chloro-2,6-dinitro-4-trifluoromethylphenyl)-5-trifluoromethyl-3-chloro-2-aminopyridine, 1-((bis(4-fluorophenyl)methylsilyl) methyl)-1H-1,2,4-triazole, 2-(4-chlorophenyl)-3-cyclopropyl-1-(1H-1,2,4-triazol-1-yl)butan-2-ol, 3-chloro-4-[4-methyl-2-(1H-1,2,4-triazol-1-ylmethyl))-1,3-dioxolan-2-yl]phenyl 4-chlorophenyl ether, [2,3-(2,4,4-trimethyltetrahydrofuran)]-1,3-dimethyl-5-chloropyrazole-4carboxanilide [sic], (2,6-dibromo-2-trofluoromethoxy)-2-methyl-4-trifluoromethylthizole-5-carboxanilide [sic], [2-(4'-chlorophenyl)]-2-chloronicotinanilide, N-[(R)-1-(2,4-dichlorophenyl) ethyl]-(S)-2-cyano-3,3-dimethylbutanamide, N-[(R)-1-(4-chlorophenyl)ethyl]-(S)-2,2-cyclopropyl-2',2-dichloro-3'-methylbutanamide, 3-allyloxy-1,2-benzisothiazole 1,1-dioxide, 2,3-benzisothiadiazole-1-carboxylic acid thioester, 1,2,5,6-tetrahydropyrrolo-[3,2,1-i,j]-quinolin-4-one, 5-methyl-1,2,4-triazolo[3,4-b] benzothiazole, diidopropyl-1,3-dithiolan-2-ylidene [sic] malonate, 4-(2,2-difluoro-1,3-benzodioxol-4-yl)pyrrole-3-carbonitrile, N-(i-propoxycarbonyl)-L-valine-(R)-1-(2-napthyl)ethylamide, N-(i-propoxycarbonyl)-L-valine-(R, S)-1-(4-methylphenyl)ethylamide, strobilurins such as methyl E-methoxyimino-[a-(o-tolyloxy)-o-tolyl]acetate [sic], methyl E-2-{2-[6-(2-cyanophenoxy)pyrimidin-4-yloxy]phenyl}-3-methoxyacrylate, N-methyl-E-methoxyimino-[a-(2-phenoxyphenyl)]acetamide [sic], N-methyl-E-methoxyimino-[a-(2,5-dimethylphenoxy)-o-tolyl] acetamide [sic], methyl (E,E)-methoxy-imino-{2-[1-(3-trifluoromethylphenyl)ethylideneaminooxymethyl]-phenyl}acetate.

In addition, fungicidally active compounds of the formulae I and II may be mentioned from amongst the class of the strobilurins

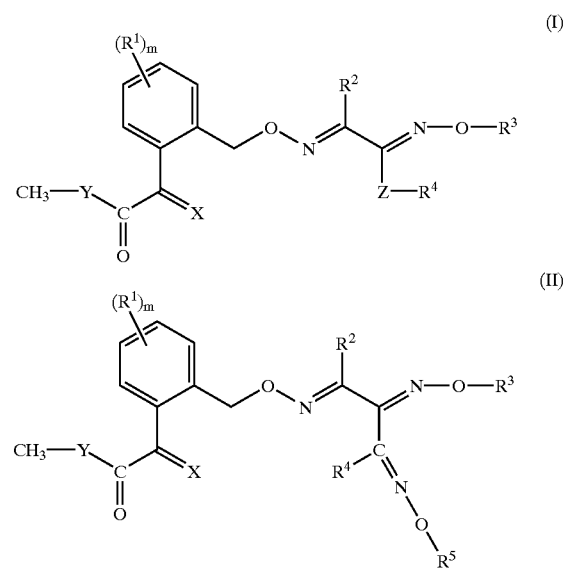

in which the substituents have the following meanings:
X is $NOCH_3$, $CHOCH_3$, $CHCH_3$;
Y is O, NH;
Z is oxygen, sulfur, amino (NH);
$R^1$ is hydrogen, cyano, nitro, trifluoromethyl, halogen, $C_1$–$C_4$-alkyl and $C_1$–$C_4$-alkoxy;
m is 0, 1 or 2, it being possible for the radicals $R^2$ to be different if m is 2;
$R^2$ is hydrogen, cyano, $C_1$–$C_4$-alkyl, $C_1$–$C_4$-haloalkyl, $C_3$–$C_6$-cycloalkyl;
$R^4$ is hydrogen,
$C_1$–$C_6$-alkyl, $C_2$–$C_6$-alkenyl, $C_2$–$C_6$-alkynyl, it being possible for the hydrocarbon radicals of these groups to be partially or fully halogenated or to have attached to them one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$- haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^7)$—$A_n$—$R^8$;

$C_3$–$C_6$-cycloalkyl, $C_3$–$C_6$-cycloalkenyl, heterocyclyl, aryl, hetaryl, it being possible for the cyclic radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy;

$R^3$, $R^5$ independently of one another are hydrogen, $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible for the cyclic groups, in turn, to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^7)$—$A_n$—$R^8$;

aryl, arylcarbonyl, arylsulfonyl, hetaryl, hetarylcarbonyl or hetarylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or $C(=NOR^7)$—$A_n$—$R^8$;

where

A is oxygen, sulfur or nitrogen and where the nitrogen has attached to it hydrogen or $C_1$–$C_6$-alkyl;

n is 0 or 1;

$R^7$ is hydrogen or $C_1$–$C_6$-alkyl and $R^8$ is hydrogen or $C_1$–$C_6$-alkyl, and their salts.

Other structures of the compounds I and II are disclosed in detail in WO 96/32015, pages 3 to 18.

When providing the mixtures, it is preferred to employ the active ingredients of the formula I or II, which may be admixed with other active ingredients against pests (for example insects, arachnids or nematodes) or harmful fungi or else herbicidal or growth-regulatory active ingredients or fertilizers, as required.

They are especially important for controlling a large number of fungi on a variety of crop plants such as cotton, vegetable plants (for example cucumbers, beans and cucurbits), barley, grass, oats, maize, fruiting plants, rice, rye, soybeans, wine, wheat, ornamentals, sugar cane, and a large number of seeds. Specifically, they are suitable for controlling the following plant diseases:

Alternaria species on vegetables and fruit,

*Botrytis cinerea* (gray mold) on strawberries, vegetables, ornamentals and grapevines,

*Cercospora arachidicola* on peanuts,

*Erysiphe cichoracearum* and *Sphaerotheca fuliginea* on cucurbits,

*Erysiphe graminis* (powdery mildew) on cereals,

Fusarium and Verticillium species on a variety of plants,

Helminthosporium species on cereals,

Mycosphaerella species on bananas,

*Phytophthora infestans* on potatoes and tomatoes,

*Plasmopara viticola* on grapevines,

*Podosphaera leucotricha* on apples,

*Pseudocercosporella herpotrichoides* on wheat and barley,

Pseudocercosporella species on hops and cucumbers,

Pseudoperonospora species on hops and cucumbers,

Puccinia species on cereals,

*Pyricularia oryzae* on rice,

Rhizoctonia species on cotton, rice and turf,

Septoria nodorum on wheat,

*Uncinula necator* on grapevines,

Ustilago species on cereals and sugar cane, and

*Venturia inaequalis* (scab) on apples.

Preferred substances amongst the fungicides are systemic strobilurins, which may be employed as a slow-release formulation in rice growing. They should be applied as granules by broadcasting. The dust-free, homogeneous granules should sediment readily in flooded fields or, when flooding treated fields, not rise to the surface, and should be dimensionally stable and storage-stable upon use, even in warmer regions.

The rates of application for the compounds of the formula I, or II, are 2 to 0.01 kg/ha, preferably 0.5 to 0.02 kg/ha, in particular 0.25 to 0.03 kg/ha.

In general, the formulations comprise 0.1 to 80, preferably 0.5 to 40, especially preferably 1 to 20, % by weight of one of the compounds of the formula I or II.

The active ingredients are employed in a purity of 90% to 100%, preferably 95% to 100% (according to $^1$H NMR or HPLC spectrum [sic]).

The compounds of the formula I or II, their mixtures or the respective formulations are applied by treating the harmful fungi, their environment, or the materials, plants, seeds, soils, areas or spaces to be protected from fungal attack, with a fungicidally active amount of the mixture, or in the case of separate application, of the compounds of the formula I or II. Treatment may be effected before or after attack by the harmful fungi.

Preferred polymeric binders are amorphous and partially crystalline polymers and mixtures of these which can be processed thermoplastically, i.e. as a viscous melt, and which additionally have a solubility in water of less than 100 mg per liter of water at 20° C.

Examples of suitable polymeric binders are:

polyolefins such as polyethylene, polypropylene, polybutylene and polyisobutylene; vinyl polymers such as polyvinyl chloride, polyvinyl acetate, polystyrene, polyacrylonitrile, polyacrylates, polymethacrylates; polyacetals such as polyoxymethylene; polyesters such as polyhydroxybutyric acid, polyhydroxyvaleric acid, polyalkylene terephthalates, polyalkylene adipate terephthalates, polybutylene adipate terephthalates; polyester amides; polyether amides; polyamides; polyimides; polyethers; polyether ketones; polyurethanes and polycarbonates. Also copolymers of ethylene/vinyl acetate, ethylene/(meth)acrylates, styrene/acrylonitrile, styrene/butadiene, styrene/butadiene/acrylonitrile, olefin/maleic anhydride.

Figure 1:
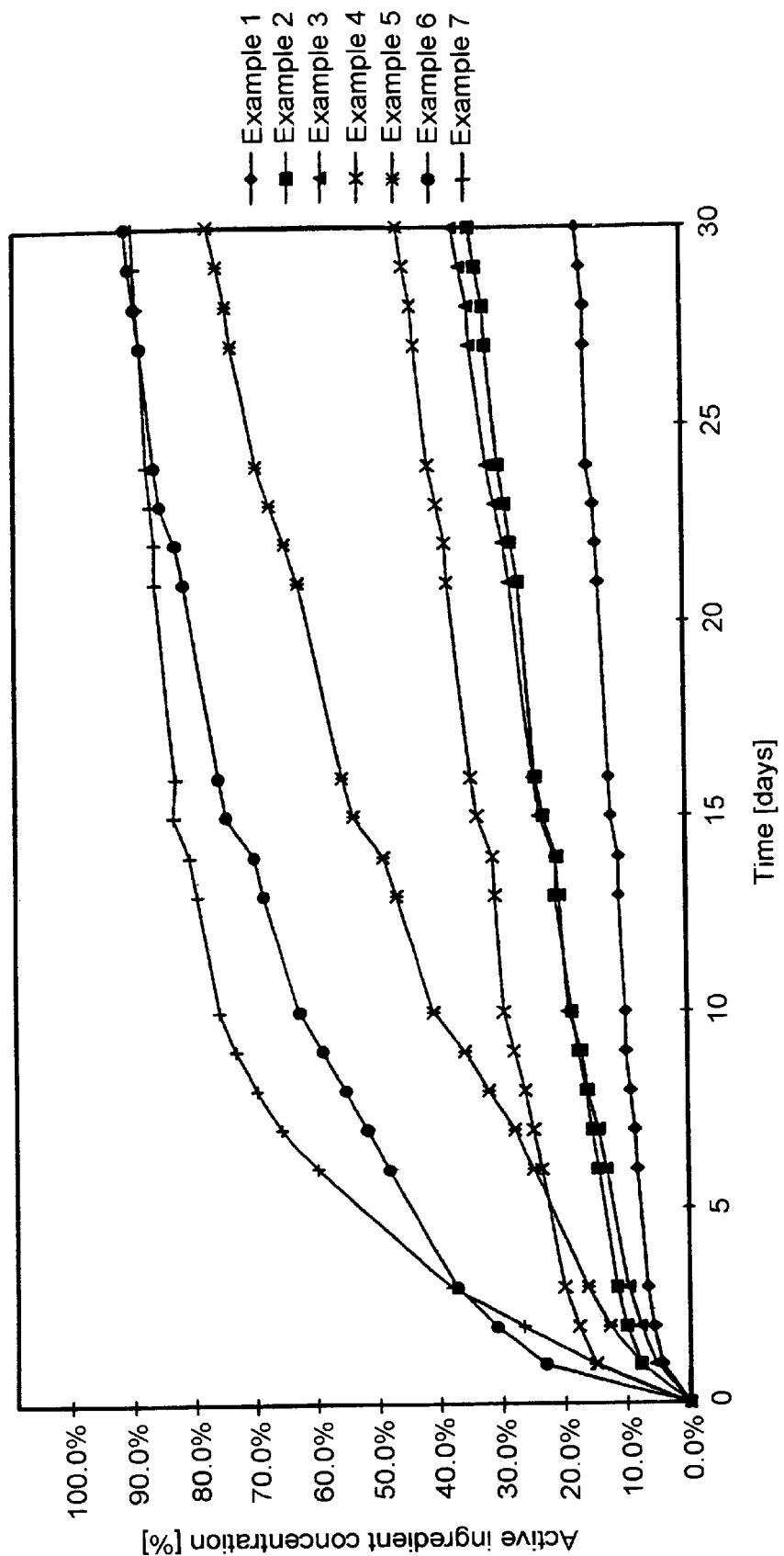
FIGS. 1–12: Depict the effects of solid crop formulation.

Examples of preferred polymers are polyolefins such as polyethylene, polypropylene and polyesters.

Especially preferred are biodegradable polybutylene adipate terephthalates, as they are described in DE 4 440 858 (Ecoflex®, BASF).

Suitable mineral fillers are substances which, due to their density, facilitate or make possible sedimentation of the granules in aqueous medium and which can be incorporated in large amounts into thermoplastic polymers, are not too hard, i.e. can be processed readily by extruding, are chemically indifferent, increase the heat resistance of the formulation, are thermostable themselves, improve the granulation properties of the melt, allow the active ingredient to be released, are ecologically sound and, moreover, as inexpensive as possible. Moreover, the incorporability of components of low viscosity, such as, for example, the active ingredient, is improved. In addition, type and amount of filler affect release of the active ingredient(s) from the polymer matrix.

It is especially the better sedimentation (high density of the mineral), the granulation properties (fillers occupy amorphous zones of the polymer and thus reduce intermolecular mobility; thus, they increase the heat resistance and reduce the elasticity; the product is easier to granulate) and the increased heat resistance that mean that the addition of a mineral filler is not only sensible from the economical standpoint, but is also necessary from the technical point of view.

Examples of suitable mineral fillers are: oxides, hydroxides, silicates, carbonates and sulfates of calcium, magnesium, aluminum and titanium; specifically for example chalk, gypsum, bentonite, kaolin, wollastonite, talc, phlogopite, clay minerals in general, and mixtures of various mineral fillers.

Preferred mineral fillers are, for example, limestone (calcium carbonate), gypsum (calcium sulfate) and talc (magnesium silicate), which are particularly suitable due to their softness and their lubricity.

The amount of mineral filler may vary within wide limits, depending on the granulation properties and the processability. Thus, the filler content may range from 10 to 80% by weight, preferably from 10 to 70% by weight, especially preferably from 10 to 60% by weight, based on the total formulation. The only condition is that the formulation can still be subjected to thermoplastic processing.

Moreover, inorganic or organic additives are optionally used to improve the processability of the mixture and to modify release of the active ingredient(s). The amount of additives should range from 0 to 20% by weight, preferably from 0 to 10% by weight and especially preferably from 0 to 5% by weight, based on the total formulation. The only condition is that the formulation can still be subjected to thermoplastic processing.

The group of additives may be divided as follows:

1) Customary auxiliaries used in extrusion technology, such as lubricants, mold release agents, fluidization auxiliaries, plasticizers and stabilizers, as they are described, for example, in DE 19504832.
2) Additives which affect release of the active ingredient(s):
    water-soluble inorganic substances such as, for example, sodium chloride, sodium sulfate or calcium sulfate
    water-soluble organic substances such as, for example, neopentyl glycol, polyethylene glycol or urea
    non-ionic or ionic surfactants such as, for example, fatty alcohol ethoxylates, alkylbenzenesulfonates or alkylnaphthalenesulfonates
    waxes, fatty alcohols and fatty acids, fats and oils such as, for example, carnauba wax, stearic acid, stearyl alcohol or castor oil To prepare the formulations according to the invention, all components can be melted together directly in the form of a physical mixture or mixed with the pre-formed polymer melt. In general, it is customary to meter into the extruder a physical mixture of active ingredient, filler, additive and polymer jointly in a free feed, e.g. via a differential weigh feeder, where it is melted.

The process steps of mixing and melting can be effected in the customary manner, for example as described in EP-A 240904, EP-A 337256 and EP-A 358195.

In general, the components are mixed in the melt in a known manner in kneaders or extruders, preferably in single- or twin-screw extruders, in a temperature range between 50 and 200° C., preferably between 50 and 150° C., especially preferably in a temperature range of between 50 and 140° C.

The extruder may contain mixing, kneading and return elements, as required. If appropriate, existing solvents and residual moisture may be stripped off during extrusion by means of gas outlet ports or vacuum pumps. Also, components in liquid and in solid form may be introduced via pumps or conveying means arranged laterally. The extrusion device used depends on the desired shape.

The melt which exits may be shaped by extrusion granulation of the fully or partially cooled extrudates, by hot cutting of the melt at the extruder head using a cut-off unit with rotating knives, by underwater granulation directly at the exit point of the melt from the nozzle, or by another method conventionally used in plastics technology described, inter alia, in EP-A 240906 and DE-A 3 830 355. The resulting solid shapes can be processed further to shaped articles, for example by injection molding.

Moreover, a layer structure can be achieved by means of coextrusion or by subsequent coating, for example in a fluidized bed, with the aid of solutions or dispersions which may comprise active ingredients and polymers, and this layer structure modulates the release of the shaped article according to the invention or incorporates an additional active ingredient component.

The process according to the invention is illustrated hereinbelow with reference to examples.

General Procedure

The amounts of active ingredient, filler, additive and polymers indicated in the examples were mixed, introduced via a weigh feeder into the conveying zone (zone 0) of a closely intermeshing counterrotating twin-screw extruder (Haake Rheocord 90 equipped with mixing screw and 2 mm nozzle, Haake, 76227 Karlsruhe) and homogenized over 5 temperature zones at a throughput of 1 kg per hour and a screw speed of 200 rpm, plastified and, at the extruder head (zone 4) discharged via a 2 mm nozzle to a metal conveyor belt. From the metal conveyor belt, the extrudate was introduced via an air chute and a Haake TP1 conveying drum, into a 1.1 mm SGS 100/E strand granulator by C.F. Scheer & CIE and formulated into cylindrical granules of average cross section 1.0–1.2 mm.

The temperature course in extruder (zones 0–4) and granulator of the examples which follow can be seen from the table which follows:

|  | Zone 0 | Zone 1 | Zone 2 | Zone 3 | Zone 4 | Granulator |
|---|---|---|---|---|---|---|
| Temperature in [° C.] | 25 | 130 | 130 | 130 | 130 | 30 |

The following starting materials were used:
Active ingredients:
Compound 1: N-methyl-2-[2-(2-isopropoxy-2-(Z)-methoxyimino-1-methyl-(E)-ethylideneaminooxymethyl) phenyl]-2-(E)-methoxyiminoacetamide Solubility in water: 1.34 g/l, melting point: 57° C.
Compound 2: N-methyl-2-[2-(2-sec-butoxy-2-(Z)-methoxyimino-1-methyl-(E)-ethyl ideneaminooxymethyl)phenyl]-2-(E)-methoxyiminoacetamide Solubility in water: 1.19 g/l, melting point: 48–50° C.
Compound 3: N-methyl-2-[2-(2-isobutoxy-2-(Z)-methoxyimino-1-methyl-(E)-ethyli deneaminooxymethyl) phenyl]-2-(E)-methoxyiminoacetamide Solubility in water: 0.5 g/l, melting point: 68° C.
Compound 4: N-methylphenyl-2-((3,4-[E]-bis (methoximino), 2-[E]-oximinopentyl)methyl)-alpha-[E]-methoximinoacetamide Solubility in water: 0.450 g/l, melting point: 91° C.
Compound 5: N-methylphenyl-2-((3-[E]-methoxyimino, 5-methyl, 2-[E]-oximino-hex-4-en-yl)methyl)-alpha-[E]-methoximinoacetamide Solubility in water: 0.058 g/l, melting point: 85° C.
Compound 6: N-(3,4-dichlorophenyl)propanamide Solubility in water: 0.13 g/l, melting point: 92° C.

Polymers
polyvinyl acetate, Vinnapas UW4, Vinnapas B5, Wacker-Chemie, DE
polyvinylpyrrolidone, Luviskol K 30, BASF AG, DE
polyvinylpyrrolidone/vinyl acetate, Luviskol VA 64, BASF AG, DE
polybutylene adipate terephthalate, Ecoflex, BASF AG, DE
polyethylene, Lupolen 1800S, BASF AG, DE Fillers/Additives
potato starch, Perfectamyl D6, AVEBE, DE
carnauba wax, Roth GmbH, DE
polyethylene glycol, Pluriol 9000, BASF AG, DE
neopentyl glycol (NPG), BASF AG, DE
calcium sulfate hemihydrate, Merck, DE
sodium chloride, Merck, DE
calcium carbonate, Merck, DE
fatty alcohol ethoxylate, Lutensol AT25, BASF AG, DE
sodium dodecylbenzenesulfonate, Aldrich, DE
stearyl alcohol, Fluka AG, Switzerland

EXAMPLE 1

Formulations based on carnauba wax/Pluriol 9000 (formulation 12–17) were not melt-extruded and granulated, due to their low melting viscosity and their low glass transition temperature. 50 g batches of the mixtures of active ingredient, carnauba wax and Pluriol 9000 were melted in a 100 ml glass flask in an oil bath at 120° C. and homogenized for 10 minutes using a glass spatula. Then, a Pasteur pipette was used to deposit drops of approx. 2–3 mm diameter on a cold metal sheet. After cooling, the wax formulations were removed from the metal sheet using a spatula.

The tables which follow list all active ingredient formulations or crop protection formulations prepared in the above-described manner, mainly by melt extrusion (formulation 1–11 and 18–67). The metered amounts in % by weight based on the total formulation can be seen from the tables:

TABLE 1

| Formulation | Compound 1 | Vinnapas B5 | Vinnapas UW4 | Luviskol K30 | Luviskol VA64 |
|---|---|---|---|---|---|
| 1 | 5 | 57 | 38 | — | — |
| 2 | 5 | 54 | 36 | 5 | — |
| 3 | 5 | 54 | 36 | — | 5 |
| 4 | 5 | 51 | 34 | 10 | — |
| 5 | 5 | 51 | 34 | — | 10 |
| 6 | 5 | 45 | 30 | 20 | — |
| 7 | 5 | 45 | 30 | — | 20 |

TABLE 2

| Formulation | Compound 1 | Lupolen 1800S | Ecoflex | Vinnapas UW4 | Perfectamyl D6 |
|---|---|---|---|---|---|
| 8 | 5 | 40 | | | 55 |
| 9 | 5 | | 40 | | 55 |
| 10 | 5 | | | 40 | 55 |
| 11 | 5 | | | 60 | 35 |

TABLE 3

| Formulation | Compound 6 | Carnauba wax | Pluriol 9000 |
|---|---|---|---|
| 12 | 5 | 76 | 19 |
| 13 | 5 | 57 | 38 |
| 14 | 5 | 38 | 57 |

TABLE 4

| Formulation | Compound 1 | Carnauba wax | Pluriol 9000 |
|---|---|---|---|
| 15 | 5 | 76 | 19 |
| 16 | 5 | 57 | 38 |
| 17 | 5 | 38 | 57 |

TABLE 5

| Formulation | Compound 6 | Lupolen 1800S | Calcium carbonate | Calcium sulfate | Sodium chloride |
|---|---|---|---|---|---|
| 18 | 5 | 40 | 45 | | 10 |
| 19 | 5 | 50 | 35 | | 10 |
| 20 | 5 | 40 | | 45 | 10 |
| 21 | 5 | 50 | | 35 | 10 |

TABLE 6

| Formulation | Compound 6 | Lupolen 1800S | Vinnapas UW4 | Ecoflex | Calcium carbonate | NPG | Pluriol 9000 |
|---|---|---|---|---|---|---|---|
| 22 | 5 | 40 | | | 45 | 10 | |
| 23 | 5 | 40 | | | 35 | 20 | |
| 24 | 5 | 40 | | | 45 | | 10 |
| 25 | 5 | 30 | | | 55 | | 10 |
| 26 | 5 | | 40 | | 45 | | 10 |
| 27 | 5 | | | 40 | 45 | | 10 |

TABLE 7

| Formulation | Compound 5 | Lupolen 1800S | Ecoflex | Perfectamyl D6 | Calcium carbonate | Calcium sulfate |
|---|---|---|---|---|---|---|
| 28 | 5 | | 50 | 45 | | |
| 29 | 5 | | 70 | 25 | | |
| 30 | 5 | | 50 | | 45 | |
| 31 | 5 | | 70 | | 25 | |
| 32 | 5 | | 50 | | 35 | 10 |
| 33 | 5 | | 70 | | 15 | 10 |
| 34 | 5 | 50 | | | 45 | |
| 35 | 5 | 70 | | | 25 | |
| 36 | 5 | 50 | | | 35 | 10 |
| 37 | 5 | 70 | | | 15 | 10 |

TABLE 8

| Formulation | Compound 4 | Lupolen 1800S | Ecoflex | Perfectamyl D6 | Calcium carbonate | Calcium sulfate |
|---|---|---|---|---|---|---|
| 38 | 5 | | 50 | 45 | | |
| 39 | 5 | | 70 | 25 | | |
| 40 | 5 | | 50 | | 45 | |
| 41 | 5 | | 70 | | 25 | |
| 42 | 5 | | 50 | | 35 | 10 |
| 43 | 5 | | 70 | | 15 | 10 |
| 44 | 5 | 50 | | | 45 | |
| 45 | 5 | 70 | | | 25 | |
| 46 | 5 | 50 | | | 35 | 10 |
| 47 | 5 | 70 | | | 15 | 10 |

TABLE 9

| Formulation | Compound 1 | Lupolen 1800S | Ecoflex | Perfectamyl D6 | Calcium carbonate | Calcium sulfate |
|---|---|---|---|---|---|---|
| 48 | 5 | | 50 | 45 | | |
| 49 | 5 | | 70 | 25 | | |
| 50 | 5 | | 50 | | 45 | |
| 51 | 5 | | 70 | | 25 | |
| 52 | 5 | | 50 | | 35 | 10 |
| 53 | 5 | | 70 | | 15 | 10 |
| 54 | 5 | 50 | | | 45 | |
| 55 | 5 | 70 | | | 25 | |
| 56 | 5 | 50 | | | 35 | 10 |
| 57 | 5 | 70 | | | 15 | 10 |

TABLE 10

| Formulation | Compound 6 | Lupolen 1800S | Calcium carbonate | Lutensol AT25 | Sodium dodecylbenzenesulfonate | Stearyl alcohol | Carnauba wax |
|---|---|---|---|---|---|---|---|
| 58 | 5 | 50 | 45 | | | | |
| 59 | 5 | 50 | 44 | 1 | | | |
| 60 | 5 | 50 | 44 | | 1 | | |
| 61 | 5 | 50 | 44 | | | 1 | |
| 62 | 5 | 50 | 40 | | | 5 | |
| 63 | 5 | 50 | 44 | | | | 1 |
| 64 | 5 | 50 | 40 | | | | 5 |

TABLE 11

| Formulation | Compound 4 | MTI 446 | Ecoflex | Chalk |
|---|---|---|---|---|
| 65 | 7 | 2 | 41 | 50 |
| 66 | 7 | 2 | 51 | 40 |
| 67 | 7 | 2 | 61 | 30 | all in % by weight
MTI 446 = tefuranitdine (preferred insecticide XII)

The resulting granules were tested for sedimentation in water (1 g of granules in 1 l of drinking water at 20° C., vibration-proof storage for 48 h) and for storage stability (50 g of granules, storage for 14 days in sealed 100 ml vessels at 54° C. in a drying oven). Granules which float in drinking water at 20° C. after 48 hours were assessed with N for No. Granules which settle to the bottom in drinking water were assessed with Y for Yes. Granules which remain dimensionally stable and flowable after heat aging were assessed with Y for Yes. Granules which do not remain dimensionally stable and flowable, i.e. which tend to agglomerate, were assessed with N for no.

| Formulation | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Sedimentation | N | Y | Y | Y | Y | N | N | N | Y | N | N | Y | Y | N | Y |
| Storage stability | N | N | N | N | N | N | N | Y | Y | N | N | N | N | N | N |
| Formulation | 16 | 17 | 18 | 19 | 20 | 21 | 22 | 23 | 24 | 25 | 26 | 27 | 28 | 29 | 30 |
| Sedimentation | Y | N | Y | Y | Y | Y | Y | Y | Y | Y | Y | Y | N | Y | Y |
| Storage stability | N | N | Y | Y | Y | Y | Y | Y | Y | Y | Y | Y | Y | Y | Y |
| Formulation | 31 | 32 | 33 | 34 | 35 | 36 | 37 | 38 | 39 | 40 | 41 | 42 | 43 | 44 | 45 |
| Sedimentation | Y | Y | Y | Y | N | Y | N | Y | Y | Y | Y | Y | Y | Y | Y |
| Storage stability | Y | Y | Y | Y | Y | Y | Y | Y | Y | Y | Y | Y | Y | Y | Y |
| Formulation | 46 | 47 | 48 | 49 | 50 | 51 | 52 | 53 | 54 | 55 | 56 | 57 | 58 | 59 | 60 |
| Sedimentation | Y | N | Y | Y | Y | Y | Y | Y | Y | Y | Y | N | Y | Y | Y |
| Storage stability | Y | Y | Y | Y | Y | Y | Y | Y | Y | Y | Y | Y | Y | Y | Y |
| Formulation | 61 | 62 | 63 | 64 | 65 | 66 | 67 | | | | | | | | |
| Sedimentation | Y | Y | Y | Y | Y | Y | Y | | | | | | | | |
| Storage stability | Y | Y | Y | Y | Y | Y | Y | | | | | | | | |

Sedimentation of the polymer blends based on polyvinyl acetate is moderate to poor, and the blends are not stable upon heat aging (formulation 1–7), they agglomerate irreversibly to form a continuous mass.

The polymer/starch blends are of limited use regarding sedimentation and storage (formulation 8–11, 28–29, 38–39, 48–49).

The wax matrices sediment in some cases only and are in no case stable upon heat aging (formulation 12–17).

The formulations based on polymer/mineral filler have the best properties regarding sedimentation and storage stability (formulation 18–27, 30–37, 40–47, 50–64, 65–67).

EXAMPLE 2

Apart from the conditions that the formulations according to the invention are transport- and storage-stable and are capable of sedimentation regarding wind and water erosion, the formulations according to the invention should release the crop protection agents at a controlled slow rate, i.e. within a period of a few days up to a few months, depending on the active ingredient and the formula. A delayed release of active ingredient is required if a long-term activity is desired or if the active ingredients are phytotoxic. To this end, the release of active ingredient from the granules in water was determined.

To determine the release of active ingredient, 1 g of granules of each of the above formulations was introduced into a 1 l graduated flask and covered with 1 l of drinking water. The flasks were stored for 4 weeks and longer at 25° C. under vibration-proof conditions. To determine the release of active ingredient, samples were taken daily. Prior to sampling, the flask was turned by 180° and mixed to guarantee a homogeneous distribution of the active ingredient. The aqueous solutions were then measured using a UV/VIS spectroscope and returned into the flasks. Calibrating curves (absorption versus concentration) of the active ingredients were established beforehand.

The apparatus used for determination of the active ingredients was the following:

UV/VIS spectroscope, HP 8452, diode array spectrophotometer, 1 cm quartz cuvette.

The absorptions were measured at different wavelengths, depending on the absorption maximum of the various active ingredients ($\lambda$=200–250 nm).

Figure 2:
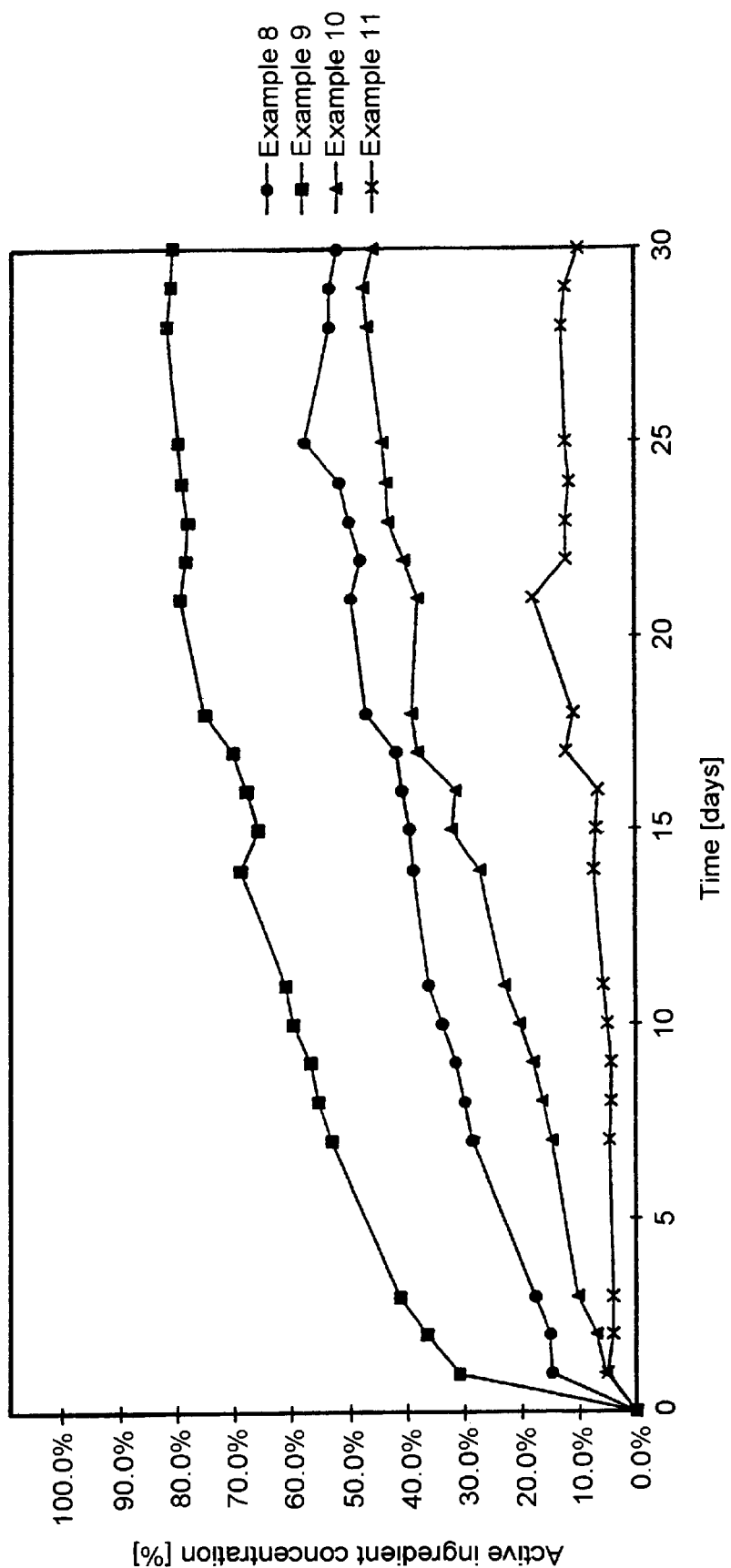
Figure 3:
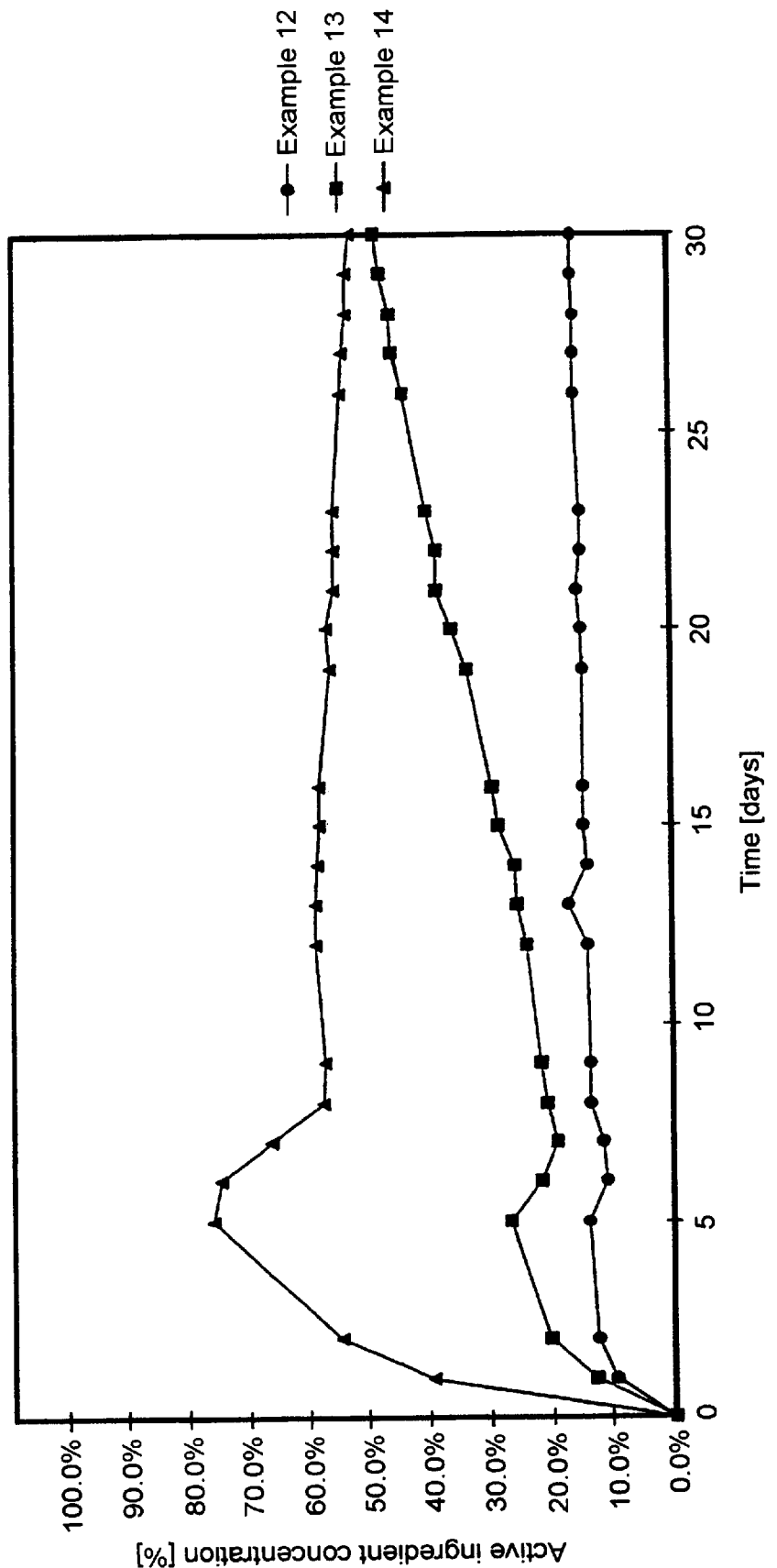
Figure 4:
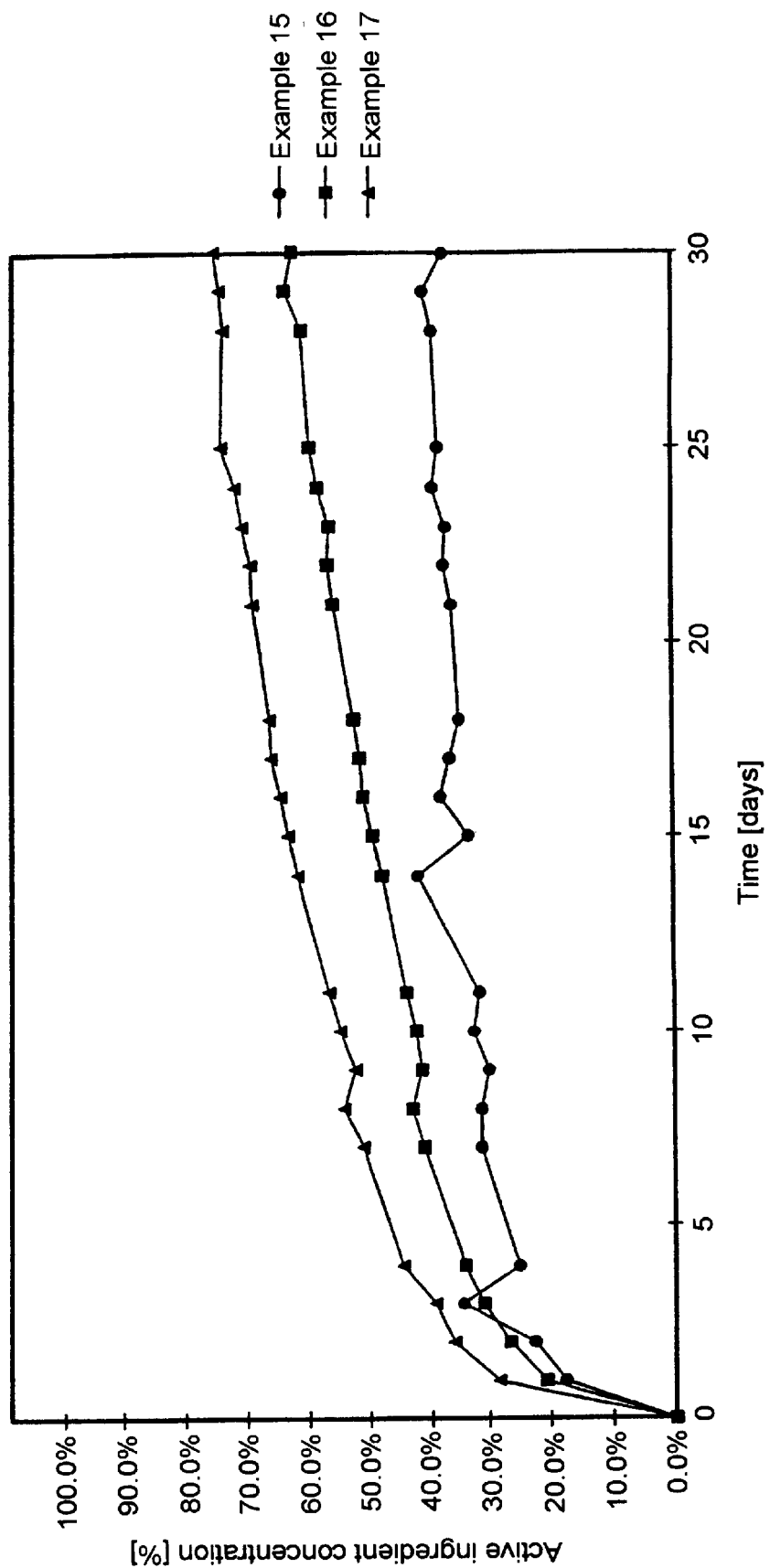
Figure 5:
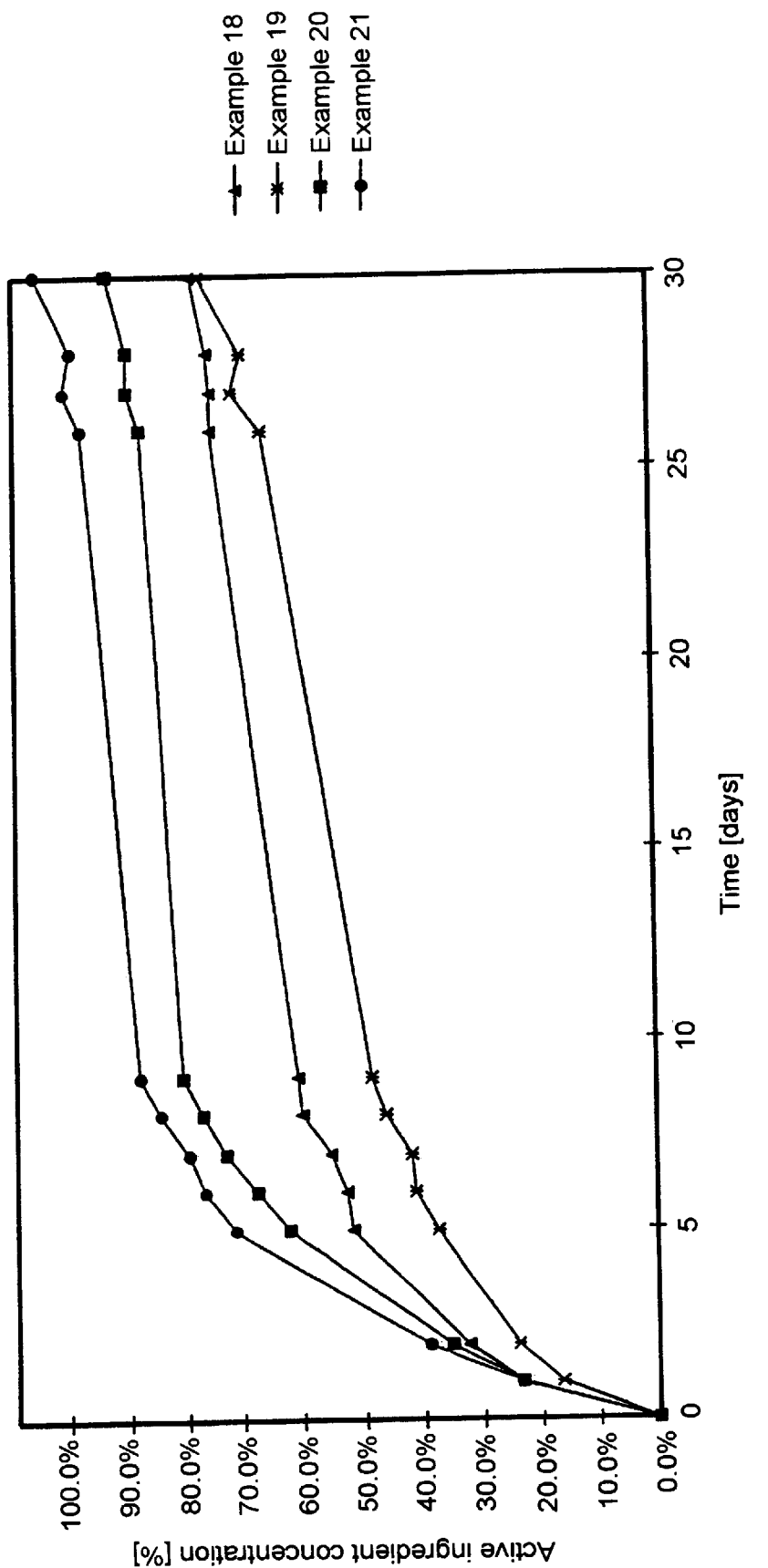
Figure 6:
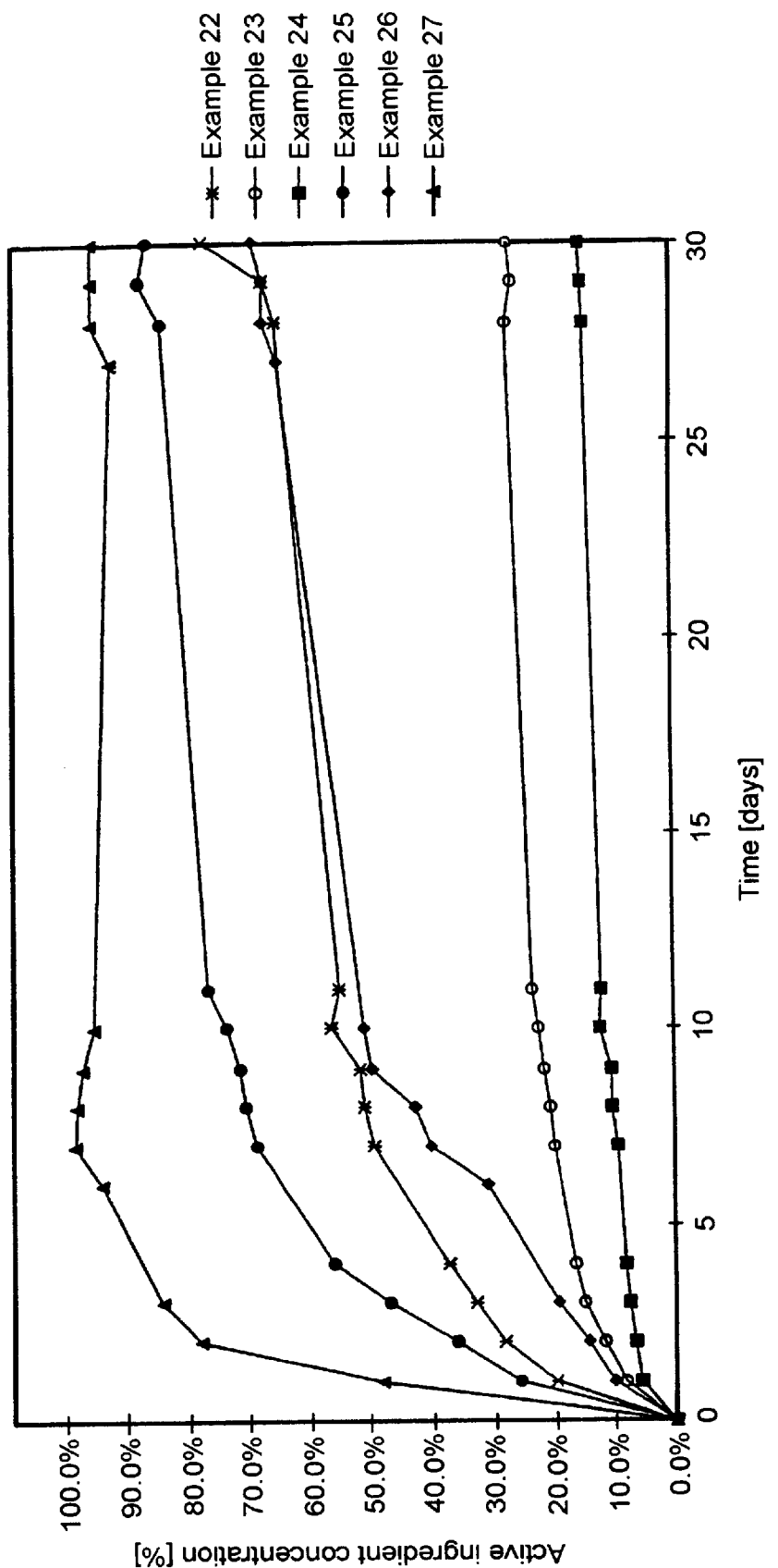
Figure 7:
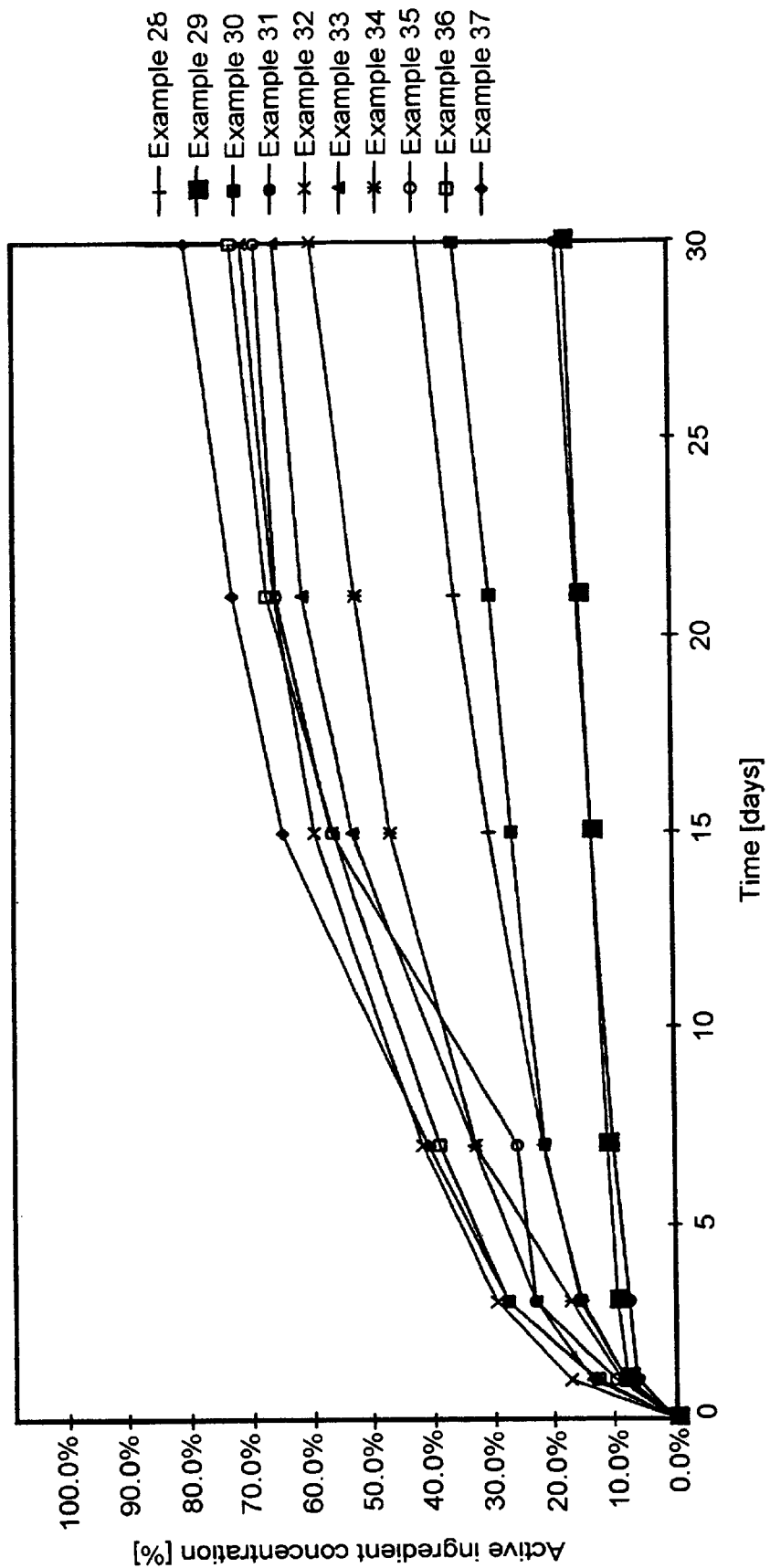
Figure 8:
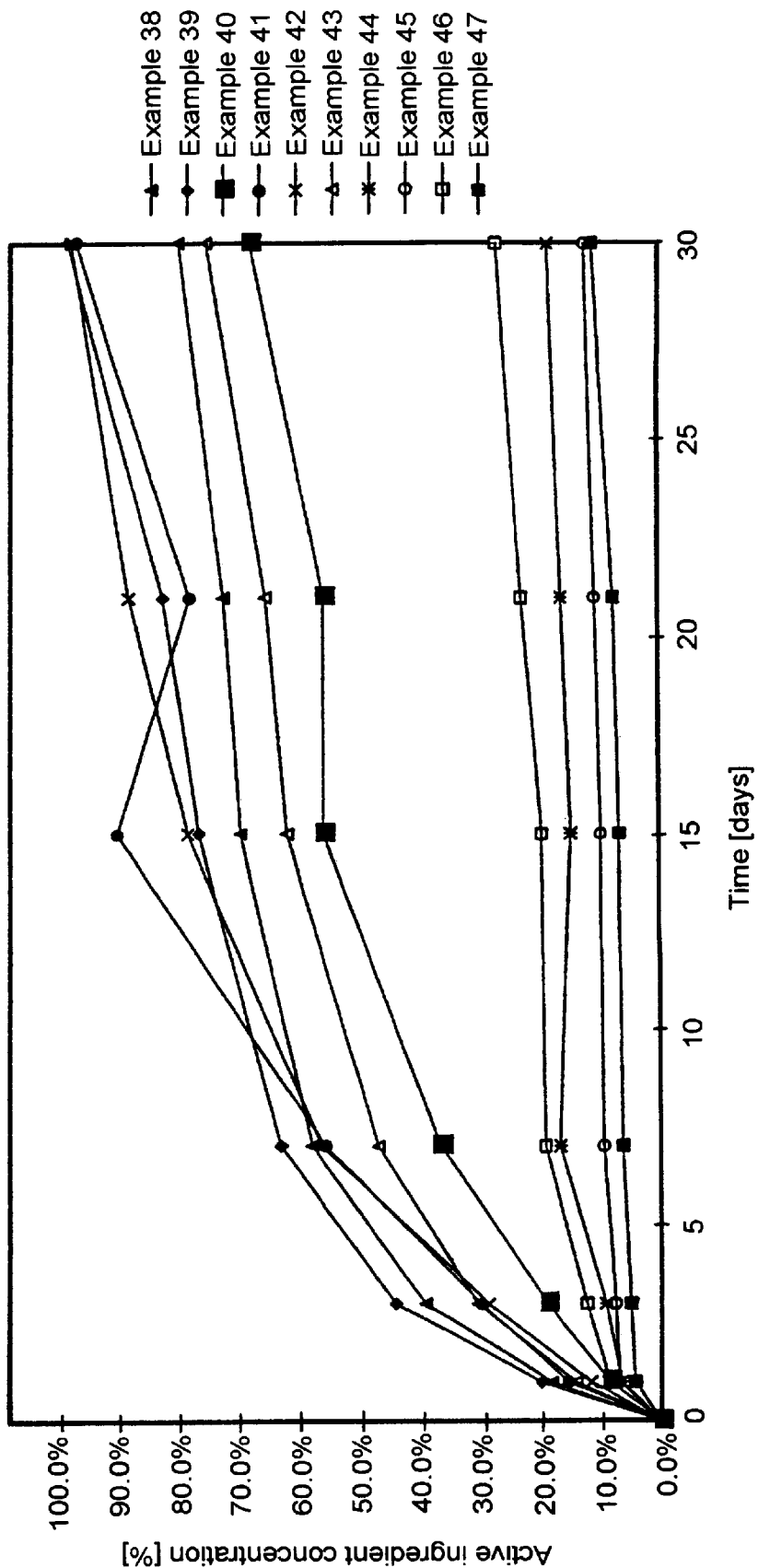
Figure 9:
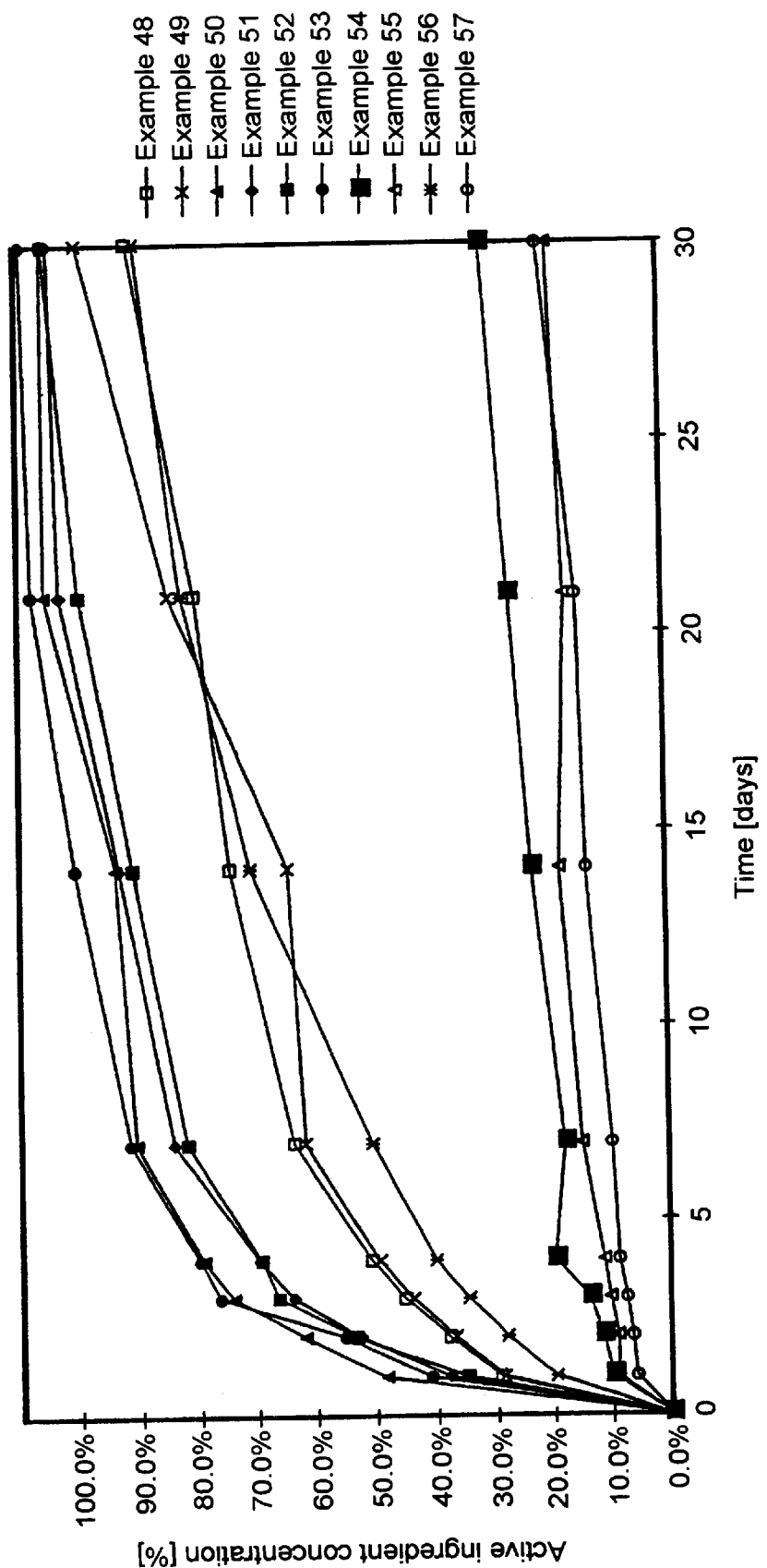
Figure 10:
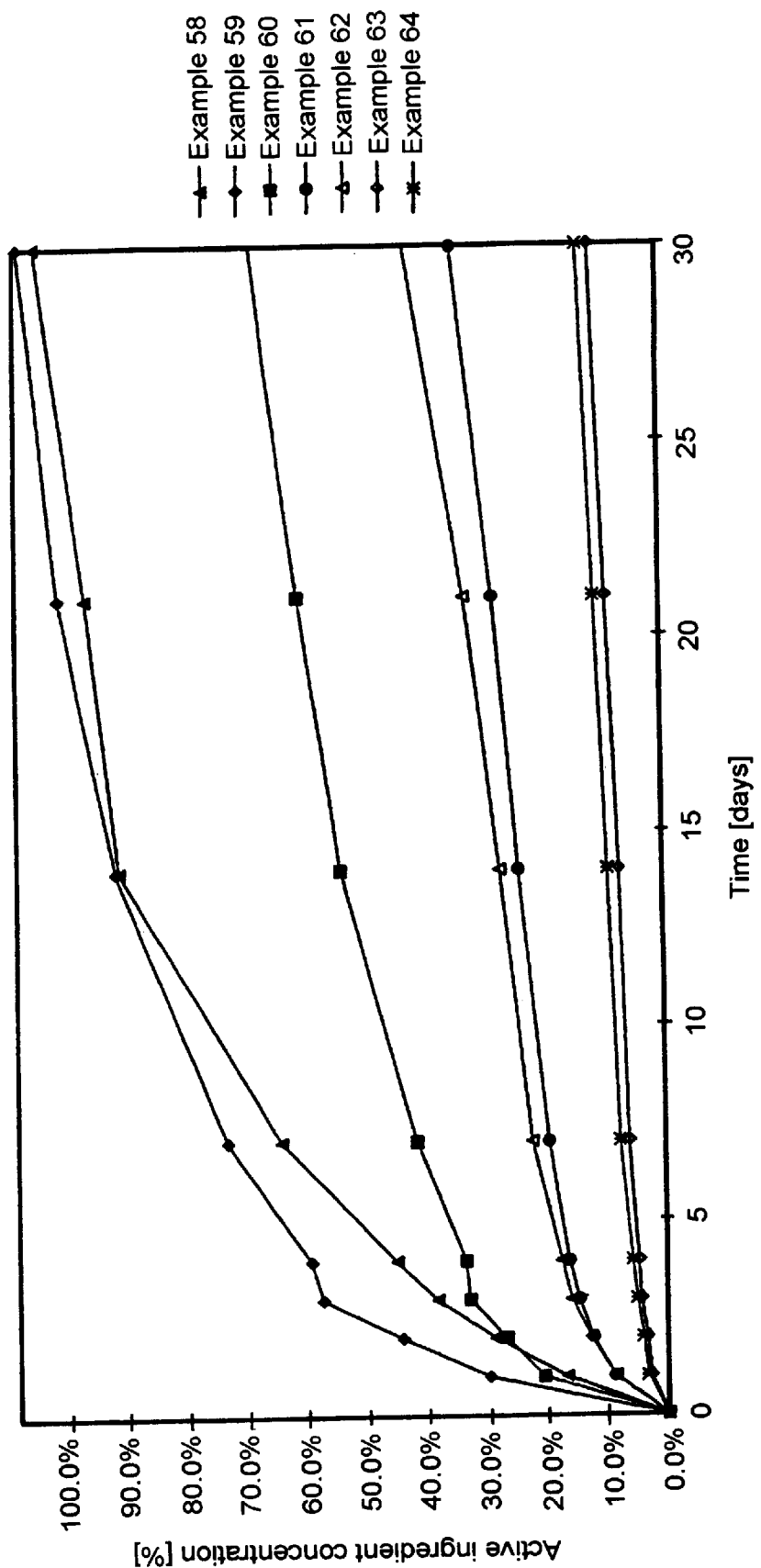
Figure 11:
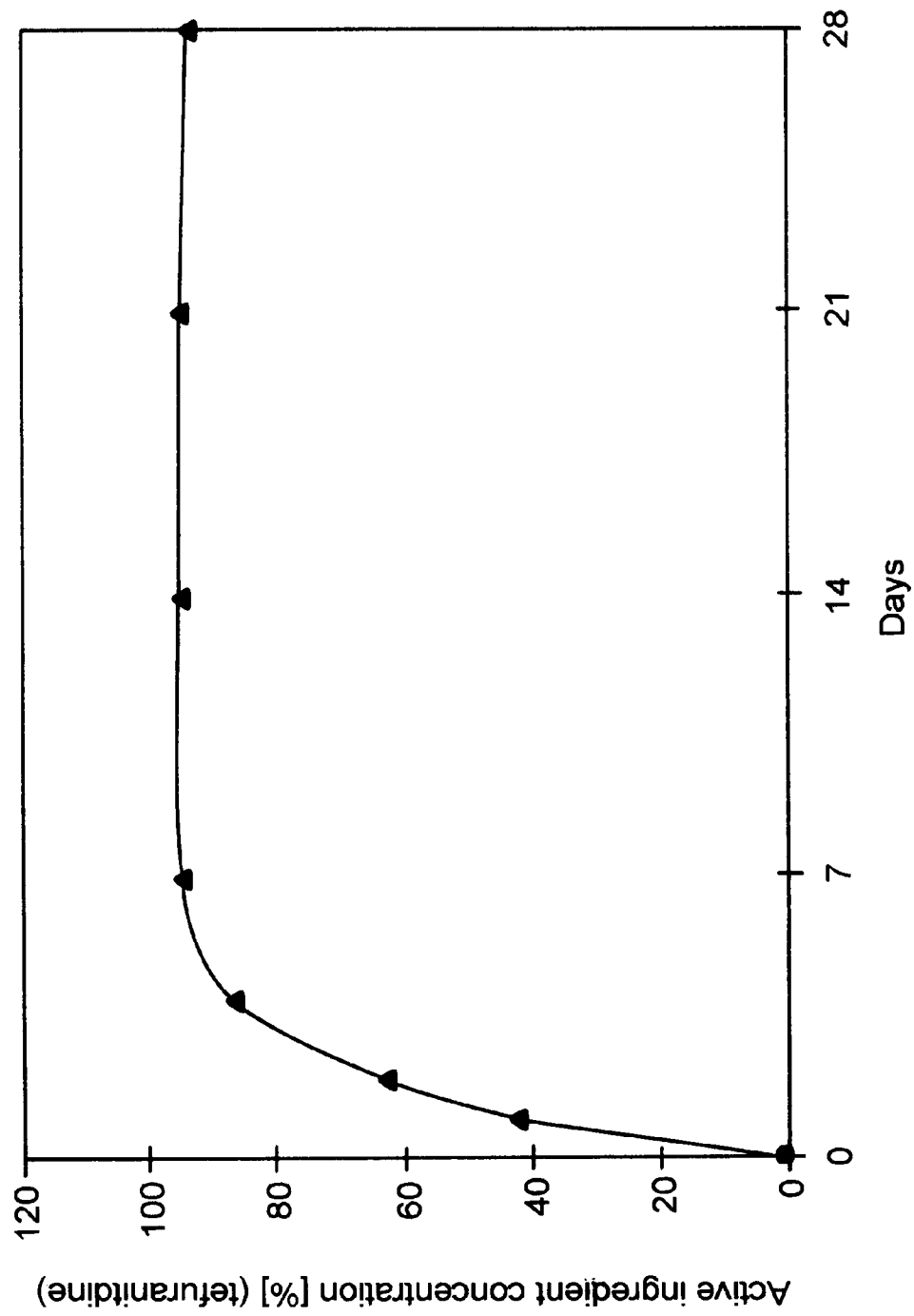
Figure 12:
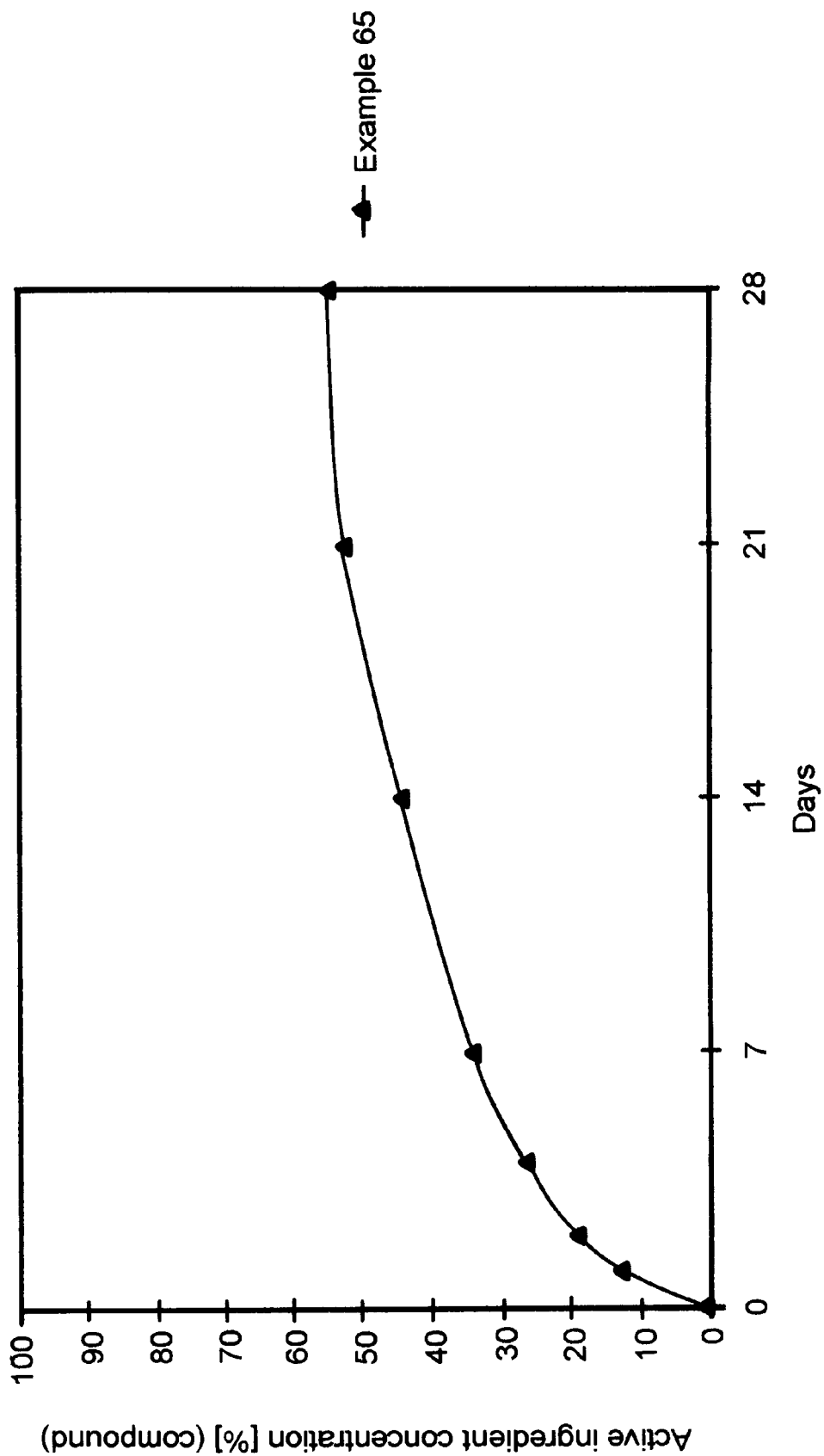

The release curves of all formulations (formulation 1–64) are found in the appendix. The percentage release was plotted against the time in days (100% means the complete release of 50 ppm of active ingredient for 1 g of 5% formulation in 1 liter of water) (see FIGS. 1–10).

The cumulated release curves of the active ingredients are square-root dependent, as can be expected for a diffusion process ($\sqrt{t}$ law):

$$c = K \times \sqrt{t}$$

t: time, c: concentration of active ingredient

Moreover, a release is highly dependent on the water solubility of the active ingredient, while its dependence on granule shape and size is less pronounced. This suggests diffusion-controlled pore diffusion. The release rate is too low for an erosion mechanism and too high for matrix diffusion. Fillers and additives affect release to the expected extent.

The release of active ingredient as a function of time can be adjusted to suit the specific aims by varying the amounts of polymer matrix, filler and, if appropriate, additive.

We claim:

1. A solid formulation of a crop protection product with delayed release of the active ingredient, obtainable by preparing a melt comprising
   0.1–80% by wt. of an active ingredient which can be used in crop protection, or of a combination of said active ingredients,
   10–80% by wt. of at least one mineral filler,
   0–20% by wt. of inorganic or organic additives, and
   to 100% by wt. of at least one thermoplastic water-insoluble polymer selected from the group consisting of polybutylene adipate terephthalates,
   the total of all constituents equaling 100% by weight, and subsequent shaping into said solid.

2. A solid formulation of said crop protection product as claimed in claim 1 comprising calcium carbonate, magnesium silicate or calcium sulfate as said mineral filler.

3. A solid formulation of said crop protection product as claimed in claim 1 comprising at least one fungicidally, herbicidally, insecticidally, acaricidally or growth-regulatory active compound or a mixture of active ingredients selected from the group of said compounds.

4. A solid formulation of said crop protection product as claimed in claim 1 comprising at least one fungicidally or herbicidally active compound or a mixture of active ingredients selected from the group of said compounds.

5. A solid formulation of said crop protection product as claimed in claim 1 comprising, as said active ingredient, at least one fungicidal compound of the formulae I and II from the class of the strobilurins

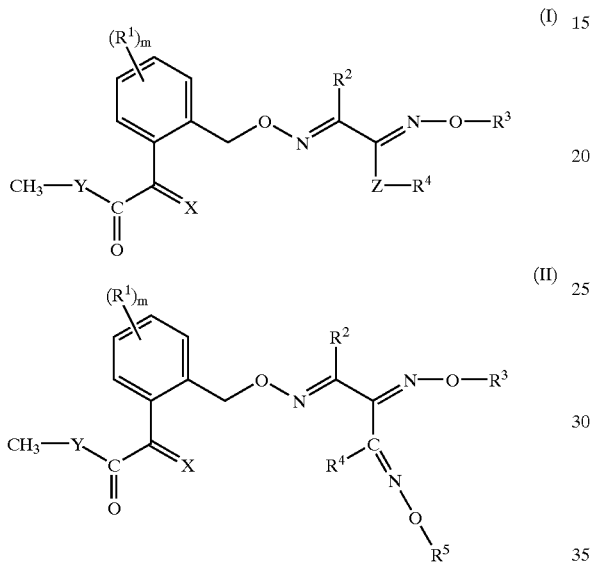

in which the substituents have the following meanings:

X is $NOCH_3$, $CHOCH_3$, $CHCH_3$;

Y is O, NH;

Z is oxygen, sulfur, amino (NH);

$R^1$ is hydrogen, cyano, nitro, trifluoromethyl, halogen, $C_1$–$C_4$-alkyl and $C_1$–$C_4$-alkoxy;

m is 0, 1 or 2, it being possible for the radicals $R^2$ to be different if m is 2;

$R^2$ is hydrogen, cyano, $C_1$–$C_4$-alkyl, $C_1$–$C_4$-haloalkyl, $C_3$–$C_6$-cycloalkyl;

$R^4$ is hydrogen,
$C_1$–$C_6$-alkyl, $C_2$–$C_6$-alkenyl, $C_2$–$C_6$-alkynyl, it being possible for the hydrocarbon radicals of said groups to be partially or fully halogenated or to have attached to them one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetatyl, hetaryloxy, hetarylthio and $C(=NOR^7)$—$A_n$—$R^8$;

$C_3$–$C_6$-cycloalkyl, $C_3$–$C_6$-cycloalkenyl, heterocyclyl, aryl, hetaryl, it being possible for the cyclic radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy;

$R^3$, $R^5$ independently of one another are hydrogen,
$C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible for the cyclic groups, in turn, to be partially or fully halogenated or to have attached to them one to three of the following: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^7)$—$A_n$—$R^8$;

aryl, arylcarbonyl, arylsulfonyl, hetaryl, hetarylcarbonyl or hetarylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or $C(=NOR^7)-A_n-R^8$, where A is oxygen, sulfur or nitrogen and where the nitrogen has attached to it hydrogen or $C_1$–$C_6$-alkyl;

n is 0 or 1;

$R^7$ is hydrogen or $C_1$–$C_6$-alkyl and $R^8$ is hydrogen or $C_1$–$C_6$-alkyl, and their salts.

6. A process for the preparation of said solid formulation of said crop protection product as claimed in claim 1 which comprises melting at least one active ingredient, at least one mineral filler, at least one thermoplastic polymer which is insoluble in water from the group consisting of polybutylene adipate terephthalates and, if appropriate, customary additives in an extruder to give a plastic mixture and dividing the melt directly or in a subsequent step to give shapes which are solid or still retain plasticity.

7. A method of controlling phytopathogenic fungi, undesired vegetation, undesired attack by insects or mites and/or for the regulation of plant growth, which comprises applying a solid formulation of a crop protection product as claimed in claim 1 to plants, their environment or to seed.

8. A method of controlling phytopathogenic fungi, undesired vegetation, undesired attack by insects or mites and/or for the regulation of plant growth, which comprises applying said solid formulation of said crop protection product as claimed in claim 1 as granules for spreading to soils which are always or temporarily flooded with water.

9. A method of controlling phytopathogenic fungi, undesired vegetation, undesired attack by insects or mites and/or for the regulation of plant growth, which comprises spreading a solid formulation of a crop protection product in the form of granules as claimed in claim 1 on plants, their environment or on seed, whenever controlled release of the active ingredient(s) is required.

* * * * *

UNITED STATES PATENT AND TRADEMARK OFFICE
CERTIFICATE OF CORRECTION

PATENT NO. : 6,541,425 B1
DATED : April 1, 2003
INVENTOR(S) : Ernst et al.

It is certified that error appears in the above-identified patent and that said Letters Patent is hereby corrected as shown below:

Column 20,
Line 55, "of said active" should be -- of such active --;
Line 61, delete "selected";
Line 64, delete "into said solid".
Line 65, "of said crop" should be -- of a crop --;
Line 67, delete "said".

Column 21,
Line 1, "of said crop" should be -- of a crop --;
Line 5, "said" should be -- these --;
Line 6, "said" should be -- a --;
Line 11, delete "said";
Line 50, "said" should be -- these --.

Column 22,
Line 14, "hetatyl" should be -- hetaryl --.

Column 23,
Line 26, "of said solid" should be -- of a solid --;
Line 27, "said" should be -- a --; insert a comma after "claim 1".

Column 24,
Line 16, "said" should be -- a --, both occurrences.

Signed and Sealed this

Nineteenth Day of August, 2003

JAMES E. ROGAN
*Director of the United States Patent and Trademark Office*